(12) United States Patent
Benbow et al.

(10) Patent No.: US 7,202,245 B2
(45) Date of Patent: Apr. 10, 2007

(54) SUBSTITUTED 4-AMINO[1,2,4]TRIAZOLO[4,3-A]QUINOXALINES

(75) Inventors: John W. Benbow, Norwich, CT (US); Margaret Y. Chu-Moyer, Old Lyme, CT (US); Daniel W. Kung, Salem, CT (US)

(73) Assignee: Pfizer Inc., New York, NY (US)

( * ) Notice: Subject to any disclaimer, the term of this patent is extended or adjusted under 35 U.S.C. 154(b) by 277 days.

(21) Appl. No.: 10/805,885

(22) Filed: Mar. 22, 2004

(65) Prior Publication Data

US 2004/0192698 A1 Sep. 30, 2004

Related U.S. Application Data

(60) Provisional application No. 60/458,500, filed on Mar. 27, 2003.

(51) Int. Cl.
- *A01N 43/58* (2006.01)
- *A01N 43/60* (2006.01)
- *A61K 31/50* (2006.01)
- *A61K 31/495* (2006.01)
- *C07D 495/00* (2006.01)

(52) U.S. Cl. ...................... 514/250; 544/346
(58) Field of Classification Search ............... None
See application file for complete search history.

(56) References Cited

FOREIGN PATENT DOCUMENTS

| EP | 1050535 | 11/2000 |
|----|---------|---------|
| EP | 1295885 | 3/2003 |
| WO | WO 0250079 | 6/2002 |
| WO | WO 02083140 | 10/2002 |

OTHER PUBLICATIONS

Hans Bundgaard, Design of Prodrugs, p. 1. © 1985 Elsevier Science Publishers.*
Richard B. Silverman, The Organic Chemistry of Drug Design and Drug Action, pp. 352-400. © Academic Press, Inc.*
Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Eldar-Finkelman and Ilouz "Challenges and opportunities with glycogen synthase kinase-3 inhibitors for insulin resistance and Type 2 diabetes treatment" Expert Opinion on Investigational Drugs, vol. 12(9), pp. 1511-1519 (2003).*

Martinez et al, "Glycogen Synthase Kinase 3 (GSK-3) Inhibitors as New Promising Drugs for Diabetes, Neurodegeneration, Cancer, and Inflammation" Medical Research Reviews, vol. 22(4), pp. 373-384 (2002).*
Singh, P. et al., Indian Journal of Chemistry, vol. 35B, pp. 929-934, Sep. 1996, "Fujita-Ban and Hansch analyses $A_1$- and $A_2$-adenosine receptor binding affinities of some 4-amino[1,2,4]triazolo[4,3-α]quinoxalines."
Sarges, R. et al., J. Med. Chem., vol. 33, pp. 2240-2254, 1990, "4-Amino[1,2,4]triazolo[4,3-α]quinoxalines. A Novel Class of Potent Adenosine Receptor Antagonists and Potential Rapid-Onset Antidepressants."
Adenot, M. et al., Eur J Med Chem, vol. 32, pp. 493-504, 1997, "Interest of cluster significance analysis in structure-affinity relationships for non-xanthine heterocyclic antagonists of adenosine."
Colotta, V. et al., Arch. Pharm. Pharm. Med. Chem., vol. 332, pp. 39-41, (1999), "4-Amino-6-benzylamino-1,2-dihydro-2-phenyl-1,2,4-triazolo[4,3-α]-quinoxalin-1-one: A New $A_{2A}$ Adenosine Receptor Antagonist with High Selectivity versus A1 Receptors."
Colotta, V. et al., J. Med. Chem., vol. 43, pp. 1158-1164, 2000, "1,2,4-Triazolo[4,3-α]quinoxalin-1-one: A Versatile Tool for the Synthesis of Potent and Selective Adenosine Receptor Antagonists."
Smith, David et al., 3-Anilino-4-arylmaleimides: Potent and Selective Inhibitors of Glycogen Synthase Kinase-3 (GSK-3), Pergamon Bioorganic & Medicinal Chemistry Letters 11 (2001) pp. 635-639.
Bertrand, J.A., et al., Structural Characterization of the GSK-3B Active Site Using Selective and Non-selective ATP-mimetic Inhibitors, J.Mol.Biol. (2003) 333, 393-407.

* cited by examiner

*Primary Examiner*—Zachary C. Tucker
(74) *Attorney, Agent, or Firm*—Ye Hua; Stephen D. Prodnuk; Bryan C. Zielinski

(57) ABSTRACT

The present invention provides compounds of formula (I)

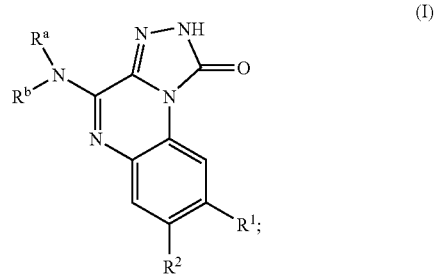

the prodrugs thereof, and the pharmaceutically acceptable salts of the compounds and prodrugs, wherein $R^a$, $R^b$, $R^1$, and $R^2$ are as defined herein; pharmaceutical compositions thereof; and uses thereof.

9 Claims, No Drawings

SUBSTITUTED 4-AMINO[1,2,4]TRIAZOLO[4,3-A] QUINOXALINES

This application claims priority to U.S. Provisional Application Ser. No. 60/458,500, filed Mar. 27, 2003.

FIELD OF THE INVENTION

The invention relates to substituted 4-amino[1,2,4]triazolo[4,3-a]quinoxalines which are inhibitors of glycogen synthase kinase-3 (GSK-3) and, as such, are useful in the treatment of, inter alia, conditions, diseases, and symptoms such as diabetes, dementia, Alzheimer's Disease, bipolar disorder, stroke, schizophrenia, depression, hair loss, cancer, and the like.

BACKGROUND OF THE INVENTION

Glycogen synthase kinase-3 (GSK-3), a proline-directed, serine/threonine kinase for which two isoforms; GSK-3α and GSK-3β, have been identified, phosphorylates the rate-limiting enzyme of glycogen synthesis, glycogen synthase (GS). See, for example, Embi, et al., Eur. J. Biochem., 107, 519–527 (1980). GSK-3α and GSK-3β are both highly expressed in the body. See, for example, Woodgett, et al., EMBO, 9, 2431–2438 (1990) and Loy, et al., J. Peptide Res., 54, 85–91 (1999). Besides GS, a number of other GSK-3 substrates have been identified, including many metabolic, signaling, and structural proteins. Notable among the plurality of signaling proteins regulated by GSK-3 are many transcription factors, including activator protein-1; cyclic AMP response element binding protein (CREB); the nuclear factor (NF) of activated T-cells; heat shock factor-1; β-catenin; c-Jun; c-Myc; c-Myb; and NF-$_{KB}$. See, for example, C. A. Grimes, et al., Prog. Neurobiol., 65, 391–426 (2001), H. Eldar-Finkelman, Trends in Molecular Medicine, 8, 126–132 (2002), and P. Cohen, et al., Nature, 2, 1–8, (2001). Accordingly, targeting the activity of GSK-3 has significant therapeutic potential in the treatment of many disparate pathologies and conditions, for example, Alzheimer's Disease (A. Castro, et al., Exp. Opin. Ther. Pat., 10, 1519–1527 (2000)); asthma (P. J. Barnes, Ann. Rev. Pharmacol. Toxicol., 42, 81–98 (2002)); cancer (Beals, et al., Science, 275, 1930–1933 (1997), L. Kim, et al., Curr. Opin. Genet. Dev., 10, 508–514 (2000), and Q. Eastman, et al., Curr. Opin. Cell Biol., 11, 233 (1999)); diabetes and its related sequelae, for example, Syndrome X and obesity (S. E. Nikoulina, et al., Diabetes, 51, 2190–2198 (2002), Orena, et al., JBC, 15765–15772 (2000), and Summers, et al., J. Biol. Chem., 274 17934–17940 (1999)); hair loss (S. E. Millar, et al., Dev. Biol., 207, 133–149 (1999) and E. Fuchs, et al., Dev. Cell, 1, 13–25 (2001)); inflammation (P. Cohen, Eur. J. Biochem., 268, 5001–5010 (2001)); mood disorders, such as depression (A. Adnan, et al., Chem. Rev., 101, 2527–2540 (2001) and R. S. B. Williams, et al., Trends Phamacol. Sci., 21, 61–64 (2000)); neuronal cell death and stroke (D. A. E. Cross, et al., J. Neurochem., 77, 94–102 (2001) and C. Sasaki, et al., Neurol. Res., 23, 588–592 (2001)); bipolar disorder (Klein, et al., PNAS, 93, 8455–8459 (1996)); skeletal muscle atrophy (G. J. Brunn, et al., Science, 277, 99–101 (1997), R. E. Rhoads, J. Biol. Chem., 274, 30337–30340 (1999), V. R. Dharmesh, et al., Am. J. Physiol. Cell Physiol. 283, C545–551 (2002), and K. Baar, et al., A. J. Physiol., 276, C120–C127 (1999)); decreased sperm motility (Vijayaraghavan, et al., Biol. Reproduction, 54, 709–718 (1996)); and in cardio-protection (C. Badorff, et al., J. Clin. Invest., 109, 373–381 (2002), S. Haq, et al., J. Cell Biol., 151, 117–129 (2000), and H. Tong, et al., Circulation Res., 90, 377–379 (2002)).

SUMMARY OF THE INVENTION

The present invention provides compounds of formula (I)

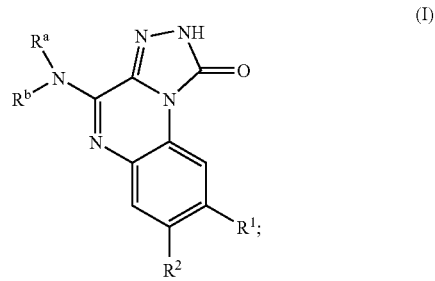

the prodrugs thereof, and the pharmaceutically acceptable salts of the compounds and prodrugs, wherein $R^a$, $R^b$, $R^1$, and $R^2$ are as defined herein; pharmaceutical compositions thereof; and uses thereof.

DETAILED DESCRIPTION OF THE INVENTION

The present invention relates to compounds of formula (I)

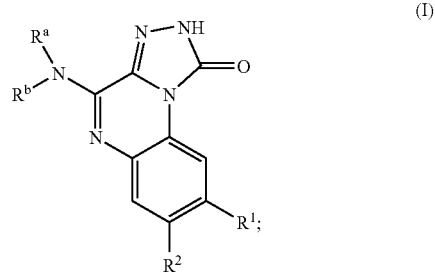

the prodrugs thereof, and the pharmaceutically acceptable salts of the compounds and prodrugs, wherein:

$R^a$ and $R^b$ are, independently:
(i) hydrogen;
(ii) acetyl;
(iii) —($C_1$–$C_6$)alkyl, optionally, and independently, substituted with from 1–3 of:
(a) halogen; (b) —$NR^3R^4$; (c) —$COR^5$; (d) —$OR^6$;. (e) aryl, optionally, and independently, substituted with from 1–3 of halogen; —($C_1$–$C_6$)alkyl; or —($C_1$–$C_6$)alkoxy; (f) heteroaryl, optionally, and independently, substituted with from 1–3 of trifluoromethyl or —($C_1$–$C_6$)alkyl; (g) —($C_3$–$C_{11}$)cycloalkyl; or (h) —($C_3$–$C_{11}$)heterocycloalkyl, optionally, and independently, substituted with from 1–3 of —($C_1$–$C_6$)alkyl or —($C_1$–$C_6$)alkoxy; wherein:

$R^3$ and $R^4$ are independently:
(j) hydrogen; (k) amidino; (l) aryl, optionally, and independently, substituted with from 1–3 of halogen; cyano; nitro; —($C_1$–$C_6$)alkyl, —($C_1$–$C_6$)alkoxy, or —$COR^5$; (m) —($C_1$–$C_6$)alkyl, optionally, and independently, substituted with from 1–3 of —($C_3$–$C_{11}$)heterocycloalkyl; —($C_3$–$C_{11}$) cycloalkyl; —($C_1$–$C_6$)alkoxy; aryl; or heteroaryl; (n) heteroaryl, optionally, and independently, substituted with from 1–3 of halogen; trifluoromethyl; cyano; nitro; —COR$^5$; —(C$_1$–C$_6$)alkyl, optionally substituted with —(C$_3$–C$_{11}$)heterocycloalkyl; or —(C$_1$–C$_6$)alkoxy; (o) —(C$_3$–C$_{11}$)heterocycloalkyl, optionally substituted with from 1–3 of —(C$_1$–C$_6$)alkyl; or (p) —COR$^5$;

R$^5$ is (q) hydroxy; (r) —(C$_1$–C$_6$)alkyl, optionally, and independently, substituted with from 1–3 of —(C$_1$–C$_6$)alkoxy or aryl; (s) —(C$_1$–C$_6$)alkoxy; (t) heteroaryl; or (u) —(C$_3$–C$_{11}$)heterocycloalky, optionally substituted with from 1–3 of —(C$_1$–C$_6$)alkyl; and R$^6$ is (v) —(C$_1$–C$_6$)alkyl, optionally, and independently, substituted with from 1–3 of —(C$_1$–C$_6$)alkoxy or aryl; (w) heteroaryl; or (x) —(C$_3$–C$_{11}$)heterocycloalkyl, optionally substituted with from 1–3 of —(C$_1$–C$_6$)alkyl;

(iv) —(C$_3$–C$_{11}$)cycloalkyl; or (v) —(C$_3$–C$_{11}$)heterocycloalkyl, optionally, and independently, substituted with from 1–3 of halogen; —COR$^5$; —(C$_1$–C$_6$)alkyl; and —(C$_1$–C$_6$)alkoxy; or R$^a$ and R$^b$, taken together with the nitrogen atom to which they are attached, form a 5- or 6-membered heterocycloalkyl ring, optionally having from 1–3 additional heteroatoms independently selected from the group consisting of nitrogen, oxygen, and sulfur, wherein said 5- or 6-membered heterocycloalkyl ring is optionally, and independently, substituted with from 1–3 of halogen; —(C$_1$–C$_6$)alkyl; or heteroaryl, optionally, and independently, substituted with from 1–3 of halogen; trifluoromethyl; and cyano; and R$^1$ and R$^2$ are independently selected from the group consisting of amino; halogen; hydrogen; trifluoromethyl; nitro; —COR$^5$; —NR$^3$R$^4$; —CONR$^3$R$^4$; and —(C$_1$–C$_6$)alkyl, optionally, and independently, substituted with from 1–3 of —(C$_3$–C$_{11}$)heterocycloalkyl; —NR$^3$R$^4$; aryl; heteroaryl; or hydroxy;

provided that when R$^a$ is hydrogen, and R$^b$ is hydrogen or isopropyl, R$^1$ is not fluoro.

A generally preferred subgroup of the compounds of formula (I) comprises those compounds wherein:

R$^a$ is hydrogen;

R$^b$ is selected from the group consisting of (iii) —(C$_1$–C$_6$)alkyl, optionally substituted with: (b) —NR$^3$R$^4$, wherein R$^3$ is hydrogen and R$^4$ is heteroaryl, optionally, and independently, substituted with from 1–3 of trifluoromethyl; cyano; —(C$_1$–C$_6$)alkyl, optionally substituted with —(C$_3$–C$_{11}$)heterocycloalkyl; —(C$_1$–C$_6$)alkoxy; or —COR$^5$; (e) aryl, optionally substituted with from 1–3 halogen atoms; (f) heteroaryl; (h) —(C3–C$_{11}$)heterocycloalkyl; (iv) —(C$_3$–C$_{11}$)cycloalkyl; or (v) —(C$_3$–C$_{11}$)heterocycloalkyl;

R$^1$ is hydrogen; halogen; —COR$^5$; —CONR$^3$R$^4$; or —(C$_1$–C$_6$)alkyl, optionally, and independently, substituted with from 1–3 of —(C$_3$–C$_{11}$)heterocycloalkyl or —NR$^3$R$^4$; and R$^2$ is hydrogen; —CONR$^3$R$^4$; or —(C$_1$–C$_6$)alkyl, optionally, and independently, substituted with from 1–3 of —(C$_3$–C$_{11}$)heterocycloalkyl or —NR$^3$R$^4$.

Another generally preferred subgroup of the compounds of formula (I) comprises those compounds wherein:

R$^a$ is hydrogen;

R$^b$ is (iii) —(C$_1$–C$_3$)alkyl, optionally substituted with (b) —NR$^3$R$^4$, wherein R$^3$ is hydrogen and R$^4$ is heteroaryl, optionally, and independently, substituted with from 1–3 of trifluoromethyl; cyano; —(C$_1$–C$_6$)alkyl, optionally substituted with —(C$_3$–C$_{11}$)heterocycloalkyl; or —(C$_1$–C$_6$)alkoxy; (e) aryl; (f) heteroaryl; (h) —(C$_3$–C$_6$)heterocycloalkyl; (iv) —(C$_3$–C$_6$)cycloalkyl; or (v) —(C$_3$–C$_{11}$)heterocycloalkyl;

R$^1$ is hydrogen; fluoro; chloro; bromo; —COR$^5$, wherein R$^5$ is hydroxy or —(C$_1$–C$_6$)alkoxy; or —CONR$^3$R$^4$, wherein R$^3$ is hydrogen or —(C$_1$–C$_6$)alkyl; and R$^4$ is —(C$_1$–C$_6$)alkyl, optionally substituted with —(C$_1$–C$_6$)alkoxy; and R$^2$ is hydrogen or —CONR$^3$R$^4$, wherein R$^3$ is —(C$_1$–C$_6$) alkyl; and R$^4$ is —(C$_1$–C$_6$)alkyl, optionally substituted with —(C$_1$–C$_6$)alkoxy.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix —(C$_a$–C$_b$)alkyl indicates an alkyl moiety of the integer "a" to "b" carbon atoms, inclusive. Thus, for example, —(C$_1$–C$_6$)alkyl refers to an alkyl group of one to six carbon atoms inclusive, for example, methyl, ethyl, propyl, isopropyl, butyl, isobutyl, pentyl, isopentyl, he)yl, and the like, including all regioisomeric forms thereof, and straight and branched chain forms thereof.

The term "alkoxy" denotes straight or branched, monovalent, saturated aliphatic chains of carbon atoms bonded to an oxygen atom, wherein the alkoxy group optionally incorporates one or more double or-triple bonds, or a combination of double bonds and triple bonds. Examples of alkoxy groups include methoxy, ethoxy, propoxy, butoxy, iso-butoxy, tert-butoxy, and the like.

The term "alkyl" denotes straight, or branched, monovalent chains of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, and the like.

The term "aryl" denotes a monocyclic, or polycyclic, aromatic hydrocarbon.

Examples of aryl groups include anthracenyl, fluorenyl, phenanthrenyl, phenyl, naphthyl, and the like.

The term "cycloalkyl" denotes a saturated monocyclic, or polycyclic, cycloalkyl group, optionally fused to an aryl group, wherein the cycloalkyl group optionally incorporates one or more double or triple bonds, or a combination of double bonds and triple bonds, but which is not aromatic. Examples of cycloalkyl groups include adamantanyl, cyclopropyl, cyclobutyl, cyclopentyl, cyclohexyl, cycloheptyl, decahydronaphthalinyl, norbornanyl, and the like.

The term "halogen" represents chloro, fluoro, bromo, and iodo.

The term "heteroaryl" denotes a monocyclic, or polycyclic, aromatic hydrocarbon group wherein one or more carbon atoms have been replaced with heteroatoms selected from the group consisting of nitrogen, oxygen, and sulfur. If the heteroaryl group contains more than one heteroatom, the heteroatoms may be the same or different. Examples of heteroaryl groups include acridinyl, benzofuranyl, benzothienyl, benzimidazolyl, benzoxazolyl, benzothiazolyl, chromenyl, cinnolinyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl. phenazinyl, phthalaziriyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated monocyclic, or polycyclic, cycloalkyl group, optionally fused to an aromatic or heteroaromatic hydrocarbon group, in which at least one of the carbon atoms has been replaced with a heteroatom selected from the group consisting of nitrogen, oxygen, and sulfur. If the heterocycloalkyl group contains more than one heteroatom, the heteroatoms may be the same or different. Examples of such heterocycloalkyl groups include azabicycloheptanyl, azetidinyl, benzazepinyl, 1,3-dihydroisoindolyl, dioxolanyl, dioxanyl, carbazolyl, dioxolanyl, dithianyl, indolinyl, imidazolidinyl, morpholinyl, quinuclidinyl, phenothiazinyl, phenoxazinyl, piperazinyl, piperidyl, pyrazolidinyl, pyrrolidinyl, tetrahydrofuryl, tetrahydroindolyl, tetrahydroisoquinolinyl, tetrahydropyranyl, tetrahydroquinolinyl, tetrahydroquinoxalinyl, tetrahydrothiopyranyl, tetrahydro-2H-1,4-thiazinyl, thiazolidinyl, thiomorpholinyl, thioxanthenyl, thioxanyl, trithianyl, and the like.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "mammal" means animals including, for example, dogs, cats, cows, sheep, horses, and humans. Preferred mammals include humans of either gender.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the preparation and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e. g., an organic radical is a group of atoms that imparts characteristic properties to a compound containing it, or which remains unchanged during a series of reactions, or transformatiens.

The term "salts" refers to organic and inorganic salts of a compound of formula (I), or a prodrug thereof. These salts can be prepared in situ during the final isolation and purification of a compound, or by separately reacting a compound of formula (I), or a prodrug thereof, with a suitable organic or inorganic acid or base arid isolating the salt thus formed. Representative salts include the hydrobromide, hydrochloride, sulfate, bisulfate, nitrate, acetate, oxalate, besylate, palrnitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1–19 (1977).

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds and prodrugs of formula (I) as well as mixtures thereof, including racemic mixtures, form part of the present invention. In addition, the present invention embraces all geometric and positional isomers. For example, if a compound or prodrug of formula (I) incorporates a double bond, both the cis- and trans-forms, as well as mixtures thereof, are embraced within the scope of the invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of formula (I) may be atropisomers (e.g., substituted biaryls) and are also considered as part of the invention.

The compounds and prodrugs of formula (I) may exist in unsolvated as well as solvated forms with pharmaceutically acceptable solvents, such as water, ethanol, and the like, and it is intended that the invention embrace both solvated and unsolvated forms.

It is also possible that the compounds and prodrugs of formula (I) may exist as tautomeric isomers in equilibrium, and all such forms are embraced within the scope of the invention.

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2$H, $^3$H, $^{13}$C, $^{14}$C, $^{15}$N, $^{18}$O, $^{17}$O, $^{31}$P, $^{32}$P, 35S, $^{18}$F, and $^{36}$Cl, respectively. The compounds of formula (I), the prodrugs thereof, and the pharmaceutically acceptable salts of the compounds and prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their relative ease of preparation and facile detection. Furthermore, substitution with heavier isotopes such as deuterium, i.e., $^2$H, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Schemes and/or Examples set forth hereinbelow, by substituting an isotopically-labeled reagent for a non-isotopically-labeled reagent.

In another aspect, the invention provides methods of treating glycogen synthase kinase-3-mediated conditions, diseases, or symptoms in a mammal in need of such treatment which comprise administering to a mammal in need of such treatment a therapeutically effective amount of a compound of formula (I), a prodrug thereof, or a pharmaceutically acceptable salt of the compound or prodrJg; a pharmaceutical composition comprising a compound of formula (I), a prodrug thereof, or a pharmaceutically acceptable salt of the compound or prodrug, and a pharmaceutically acceptable carrier, vehicle, or diluent; or a combination of an amount of a compound of formula (I), a prodrug thereof, or a pharmaceutically acceptable salt of the compound or prodrug, and an amount of one or more of: (i) an anti-angiogenesis agent, (ii) a signal transduction inhibitor, (iii) an anti-proliferative agent, (iv) an NK-1 receptor antagonist, (v) a $5HT_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator; or a pharmaceutical composition comprising the aforementioned combinations.

Preferred conditions, diseases, and symptoms treatable according to the instant methods are those selected from the group consisting of Alzheimer's Disease, asthma, atherosclerosis, anxiety, bipolar disorder, cancer, diabetes, dementia, depression, frailty, hair loss, heart failure, essential hypertension, hyperglycemia, hyperlipidemia, hypoglycemia, inflammation, ischemia, male fertility and sperm motility, mood disorders, neuronal cell death, obesity, obsessive compulsive disorder, polycystic ovary disorder, schizophrenia, stroke, Syndrome X, and traumatic brain injury. An especially preferred disease treatable according to the instant methods is diabetes.

Frailty is characterized by the progressive and relentless loss of skeletal muscle mass resulting in a high risk of injury from fall, difficulty in recovery from illness, prolongation of hospitalization, and long-term disability requiring assistance in daily living. The reduction of muscle mass and physical strength typically leads to diminished quality of life, loss of independence, and mortality. Frailty is normally associated with aging, but may also result when muscle loss and reduced strength occur due to other factors, such as disease-induced cachexia, immobilization, or drug-induced sarcopenia. Another term that has been used to denote frailty is sarcopenia, which is a generic term for the loss of skeletal muscle mass, or quality. Examples of skeletal muscle properties that contribute to its overall quality include contractility, fiber size and type, fatiguability, hormone responsiveness, glucose uptake/metabolism, and capillary density.

Generally preferred anti-angiogenesis agents may comprise, for example, matrix metalloproteinase-2 (MMP-2) inhibitors, matrix metalloproteinase-9 (MMP-9) inhibitors, and cyclooxygenase-II (COX-II) inhibitors. Examples of useful MMP-2 and MMP-9 inhibitors are disclosed in, for example, PCT International Application Publication Nos. WO 98/34915 and WO 98/34918, and U.S. Pat. Nos. 5,240, 958; 5,310,763; 5,455,258; 5,506,242; 5,530,161; 5,552, 419; 5,672,615; 5,861,510; 5,863,949; 5,932,595; 5,994, 351; 6,077,864; 6,087,392; 6,090,852; 6,110,964; 6,147, 061; 6,147,074; 6,303,636; 6,380,219; and 6,387,931. Examples of COX-II inhibitors useful in the present combinations and methods comprise CELEBREX® (celecoxib, U.S. Pat. No. 5,466,823), valdecoxib (U.S. Pat. No. 5,633, 272), and rofecoxib (U.S. Pat. No. 5,474,995). Generally preferred MMP-2 and MMP-9 inhibitors are those that exhibit little or no activity inhibiting MMP-1. Especially preferred MMP-2 and MMP-9 inhibitors are those that selectively inhibit MMP-2 and/or MMP-9 relative to other MMP inhibitors, i.e., MMP-1, MMP-3, MMP-4, MMP-5, MMP-6, MMP-7, MMP-8, MMP-10, MMP-11, MMP-12, and MMP-13. Specific examples of MMP inhibitors useful in the present combinations and methods comprise AG-3340, RO 32-3555, RS 13-0830, and the following compounds:

3-[[4-(4-fluoro-phenoxy)-benzenesulfonyl]-(1-hydroxy-carbamoyl-cyclopentyl)-amino]-propionic acid;

3-exo-3-[4-(4-fluoro-phenoxy)-benzenesulfonyl-amino]-8-oxa-bicyclo[3.2.1]octane-3-carboxylic acid hydroxyamide;

(2R,3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonyl-amino]-tetrahydro-pyran-4-carboxlyic acid hydroxyamide;

3-[[4-(4-fluoro-phenoxy)-benzenesulfonyl]-(1-hydroxy-carbamoyl-cyciobutyl)-amino]-propionic acid;

4-[4-(4-chloro-pherioxy)-benzenesulfonyl-amino]-tetrahydro-pyran-4-carboxlyic acid hydroxyamide;

(R)-3-[4-(4-chloro-phenoxy)-benzenesulfonyl-amino]-tetrahydro-pyran-3-carboxlyic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxy-carbamoyl-1-methyl-ethyl)-amino]-propionic acid;

3-[[4-(4-fluoro-phenoxy)-benzenesulfonyl]-(4-hydroxy-carbamoyl-tetrahydro-pyran-4-yl)-amino[-propionic acid;

3-exo-3-[4-(4-chloro-phenoxy)-benzenesulfonyl-amino]-8-oxa-bicyclo[3.2.1 ]octane-3-carboxylic acid hydroxyamide;

3-endo-3-[4-(4-fluoro-phenoxy)-benzenesulfonyl-amino]-8-oxa-bicyclo[3.2.1]octane-3-carboxylic acid hydroxyamide; and (R)-3-[4-(4-fluoro-phenoxy)-benzenesulfonyl-amino]-tetrahydro-furan-3-carboxlyic acid hydroxyamide; and the pharmaceutically acceptable salts and solvates thereof.

Generally preferred signal transduction inhibitors may comprise, for example, epidermal growth factor receptor (EGFR) response inhibitors, such as EGFR antibodies, EGF antibodies, and molecules that are EGFR inhibitors; vascular endothelial growth factor (VEGF) inhibitors; and erbB2 receptor inhibitors, such as molecules or antibodies that bind to the erbB2 receptor, for example, HERCEPTIN® (Genentech Inc.; South San Francisco, Calif.). EGFR inhibitors are described in, for example, PCT International Application Publication No. WO 98/14451, and U.S. Pat. Nos. 5,679, 683; 5,747,498; and 6,391,874. EGFR-inhibiting agents may comprise, for example, the monoclonal antibodies C225 and anti-EGFR 22Mab (Imclone Systems, Inc.), ZD-1839, BIBX-1382, MDX-103, VRCTC-310, and EGF fusion toxin (Seragen Inc.; Hopkinton, Mass.). VEGF inhibitors are disclosed in, for example, PCT International Application Publication No. WO 99/24440, and U.S. Pat. Nos. 5,792, 783; 5,834,504; 5,851,999; 5,883,113; 5,886,020; 6,051, 593; 6,114,371; 6,133,305; 6,162,804; 6,174,889; 6,207,669; 6,235,741; 6,291,455; 6,294,532; 6,310,238; 6,380,203; and 6,395,734. Specific VEGF inhibitors may comprise, for example, Su-5416, IM862, anti-VEGF monoclonal antibody (Cytran Inc.; Kirkland, Wash.), and angiozyme (Ribozyme; Boulder, Colo.). ErbB2 receptor inhibitors are disclosed in, for example, PCT International Application Publication Nos. WO 97/13760, WO 99/35132, and WO 99/35146, and U.S. Pat. Nos. 5,679,683; 5,587,458; 5,877,305; 6,207,669; and 6,391,874. Specific erbB2 receptor inhibitors may comprise, for example, GW-282974 (Glaxo Wellcome plc.), and the monoclonal antibody AR-209 (Aronex Pharmaceuticals Inc.; The Woodlands, Tex.).

Generally preferred anti-proliferative agents may comprise, for example, cytotoxic lymphocyte antigen 4 (CTLA4) antibodies, and other agents capable of blocking CTLA4; and farnesyl transferase inhibitors.

Examples of NK-1 receptor antagonists are disclosed in, for example, U.S. Pat. Nos. 5,122,525; 5,162,339; 5,232,929; 5,332,817; 5,703,240; 5,716,965; 5,719,147; 5,744,480; 5,763,699; 5,773,450; 5,807,867; 5,843,966; 5,852,038; 5,886,009; and 5,939,433.

Examples of $5HT_{1D}$ receptor antagonists useful in the present combinations and methods are disclosed in, for example, PCT International Application Publication No. WO 94/21619, and U.S. Pat. Nos. 5,358,948; 5,510,350; 6,380,186; 6,403,592; 6,423,708; and 6,462,048.

Examples of SSRI's useful in the present combinations and methods may comprise, for example, fluoxetine (U.S. Pat. No. 4,314,081), paroxetine (U.S. Pat. No. 4,007,196), sertraline (U.S. Pat. No. 4,536,518), fluvoxamine (U.S. Pat. No. 4,085,225), venlafaxine hydrochloride (EFFEXOR®, U.S. Pat. No. 4,535,186), nefazodone hydrochloride (SERZONE®, U.S. Pat. No. 4,338,317), and bupropion hydrochloride (WELLBUTRIN®, U.S. Pat. Nos. 3,819,706 and 3,885,046).

Generally preferred anti-psychotic agents useful in the present combinations and methods may comprise, for example, ziprasidone (GEODON®, U.S. Pat. No. 5,312,925), olanzapine (U.S. Pat. No. 5,229,382), risperidone (U.S. Pat. No. 4,804,663), L-745,870, sonepiprazole, RP-62203 (fananserin), NGD-941, balaperidone, flesinoxan (U.S. Pat. No. 4,833,142), and gepirone (U.S. Pat. No. 4,423,049).

Generally preferred acetylcholinesterase inhibitors useful in the present combinations and methods may comprise, for example, donepezil (ARICEPT®, U.S. Pat. No. 4,895,841), rivastigmine (EXELON®, U.S. Pat. No. 4,948,807), metrifonate (U.S. Pat. No. 2,701,225), galanthamine, physostigmine, tacrine, huperzine, and. icopezil (U.S. Pat. No. 5,538,984).

Generally preferred neuroprotectants useful in the instant combinations and methods may comprise, for example, NMDA receptor antagonists. Specific NMDA receptor antagonists comprise, for example, (1S,2S)-1-(4-hydroxyphenyl)-2-(4-hydroxy-4-phenylpiperidin-1-yl)-1-propanol (U.S. Pat. No. 5,272,160); eliprodil (U.S. Pat. No. 4,690,931); and gavestenel (U.S. Pat. No. 5,373,018). Examples of additional NMDA antagonists are disclosed in, for example, U.S. Pat. Nos. 4,690,931; 5,185,343; 5,272,160; 5,356,905; 5,373,018; 5,744,483; 5,962,472; 6,046,213; 6,124,317; 6,124,323; 6,130,234; 6,218,404; 6,333,036; and 6,448,270; and in PCT International Application Publication Nos. WO 97/23202 and WO 98/18793.

A generally preferred potassium channel modulator comprises, for example, BMS-204352 (flindokaliner, U.S. Pat. No. 5,602,169).

The disclosures of all of the above U.S. patents are incorporated herein in their entirety by reference.

In another aspect, the invention provides methods for inhibiting glycogen synthase kinase-3 activity in a mammal in need of such inhibition which comprise administering a glycogen synthase kinase-3 inhibiting amount of a compound of formula (I), a prodrug thereof, or a pharmaceutically acceptable salt of the compound or prodrug; or a pharmaceutical composition comprising a compound of formula (I), a prodrug thereof, or a pharmaceutically acceptable salt of the compound or prodrug, and a pharmaceutically acceptable carrier, vehicle, or diluent.

The compounds of formula (I), the prodrugs thereof, and the pharmaceutically acceptable salts of the compounds and prodrugs, may be administered to a mammal at dosage levels in the range of from about 0.0001 mg to about 1,000 mg per day. For a normal adult human having a body mass of about 70 kg, a dosage in the range of from about 0.01 mg to about 500 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, the compounds of formula (I), the prodrugs thereof, and the pharmaceutically acceptable salts of the compounds and prodrugs, or the aforementioned combinations thereof with the amounts of one or more of: (i) an anti-angiogenesis agent, (ii) a signal transduction inhibitor, (iii) an anti-proliferative agent, (iv) an NK-1 receptor antagonist, (v) a $5HT_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator, are preferably administered in the form of a pharmaceutical composition comprising a pharmaceutically acceptable carrier, vehicle, or diluent. Accordingly, a compound of formula (I), a prodrug thereof, or a pharmaceutically acceptable salt of the compound or prodrug, or the aforementioned combinations, may be administered to a subject separately, or together, in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and. sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of the aforementioned substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I), the prodrugs thereof, and the pharmaceutically acceptable salts of the compounds and prodrugs, may be prepared according to the exemplary synthetic routes disclosed in the Schemes and Examples hereinbelow, as well as by other conventional organic preparative methods known, or apparent in light of the instant disclosure, to one of ordinary skill in the relevant art. It is to be understood that the methods disclosed in the instant Schemes are intended for purposes of exemplifying the instant invention, and are not to be construed in any manner as limitations thereon.

A generalized method for preparing the compounds of formula (I) is depicted in Scheme 1 hereinbelow. Alternative synthetic routes for the preparation of compounds of formula (I) wherein $R^a$, $R^b$, $R^1$, and/or $R^2$ comprise specifically enumerated functional groups are set forth hereinbelow in Schemes 2 to 5.

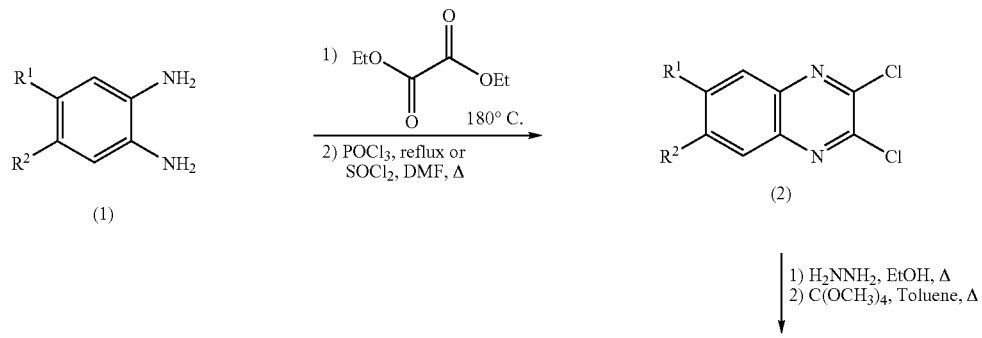

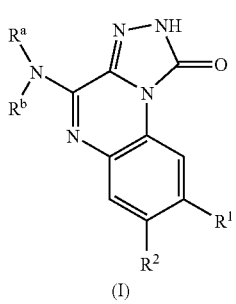

1) $R^aR^bNH$, DMF, Δ
2) HBr/AcOH, 100° C.

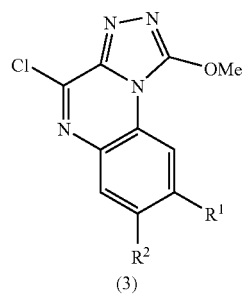

(3)

In Scheme 1, an appropriately-substituted 1,2-diaminophenyl derivative (1) is cyclocondensed with diethyl oxalate and the resulting quinoxaline-2,3-dione is heated in the presence of neat phosphorus oxychloride, or thionyl chloride and a catalytic amount of dimethylformamide (DMF), to afford the substituted 2,3-dichloroquinoxaline (2). Typically, the cyclocondensation is effected at elevated temperature, preferably at, or about, 180° C. Treatment of quinoxaline (2) with hydrazine in a protic solvent, preferably ethanol, followed by heating with tetramethyl orthocarbonate in a reaction-inert solvent, such as toluene, affords the substituted 4-chloro-1-methoxy[1,2,4]triazolo[4,3-a]quinoxaline derivative (3). Displacement of the chlorine atom of (3) with an appropriately-substituted amine $R^aR^bNH$ in DMF, followed by treatment with HBr/AcOH at elevated temperature affords (I). Alternatively, the imino ether group in compound (3) may be cleaved in the presence of a metal catalyst, preferably Pd, with a hydrogen source, such as cyclohexene, in a protic solvent, preferably methanol, or by exposure to an organic or inorganic acid, preferably HCl in dioxane.

Alternatively, the compounds of formula (I) wherein $R^a$ represents hydrogen, and $R^b$ represents —$(C_1-C_6)$alkyl, substituted with —$NR^3R^4$, wherein $R^3$ is hydrogen, and $R^4$ is, for example, heteroaryl, are conveniently prepared according to the exemplary method outlined in Scheme 2 hereinbelow.

Scheme 2

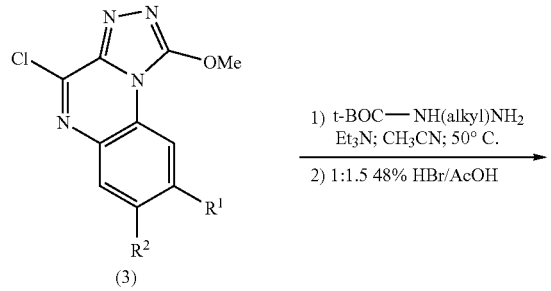

1) t-BOC—NH(alkyl)NH$_2$
   Et$_3$N; CH$_3$CN; 50° C.
2) 1:1.5 48% HBr/AcOH

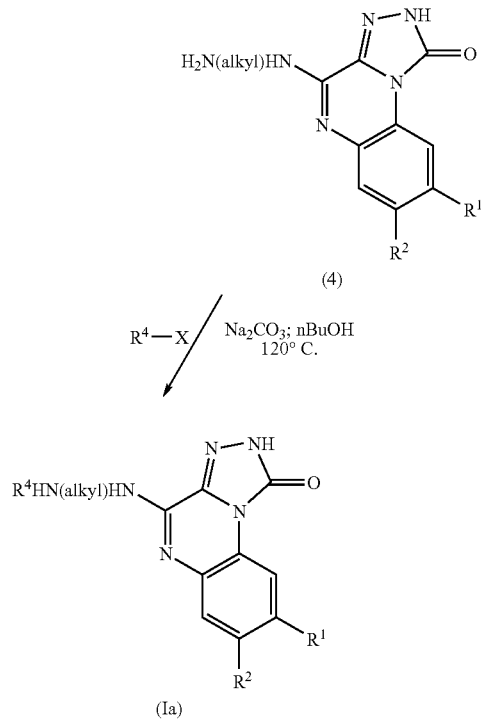

In Scheme 2, a mono-protected (preferably tert-butoxycarbonyl; t-BOC) alkylenediamine, is first reacted with a 4-chloro-1-methoxyquinoxaline derivative (3) to afford a protected diaminoquinoxaline derivative. Typically, the reaction is effected in the presence of an organic base, such as triethylamine, in a reaction-inert solvent, such as acetonitrile, at above ambient temperature. Subsequent exposure of this product to HBr/AcOH at elevated temperature removes both the imidate ether and the protecting group to provide diaminoquinoxaline (4). Reaction of (4) with $R^4$—X, wherein $R^4$ comprises, for example, a heteroaryl moiety, for example, pyridyl or pyrimidinyl, and X represents a suitable leaving group, for example, a halogen such as chlorine or bromine, affords (Ia). Normally, the reaction is performed in a high-boiling protic solvent, such as n-butanol, in the presence of an inorganic base, such as sodium carbonate. Alternatively, functionalization of (4) may also be effected wherein $R^4$ incorporates a carbonyl group, wherein X represents a chlorine atom.

Alternatively, the compounds of formula (I) wherein $R^1$ represents —$CONR^3R^4$ and —$CH_2NR^3R^4$ and $R^2$ is hydrogen are conveniently prepared according to the exemplary method shown in Scheme 3.

Scheme 3

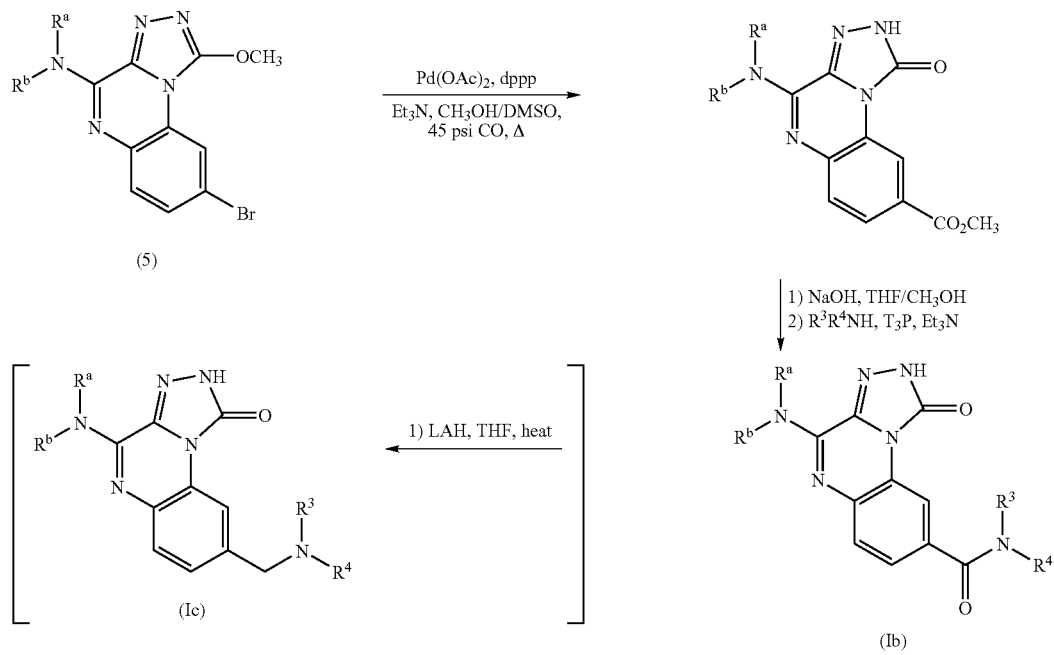

In Scheme 3 hereinabove, an 8-bromo-4-amino-1-methoxyquinoxaline derivative (5) is converted into the corresponding 8-carbomethoxy derivative under Heck Reaction conditions. Generally, a solution of (5) containing an organic base, such as triethylamine, a Pd source, preferably Pd(II) acetate and a soluble ligand, such as bis-diphenylphosphinopropane (dppp), and the alcohol precursor to the desired ester product in a polar solvent, preferably DMSO (dimethylsulfoxide), is heated under an atmosphere of carbon monoxide gas at elevated temperature, normally 45 psi. These conditions are typically sufficient to cleave the methyl ether and generate the corresponding carbonyl group in the desired product. Saponification of the resulting ester with an inorganic base, such as sodium hydroxide, in a polar, protic solvent mixture, preferably tetrahydrofuran (THF)/methanol, provides the corresponding carboxylic acid, which is converted into amide (Ib) with an appropriately-substituted amine $R^3R^4NH$, utilizing conventional coupling methodologies. Typically, a solution of the carboxylic acid and the amine $R^3R^4NH$ in an organic solvent, such as ethyl acetate, and an organic base, such as triethylamine, is treated with a coupling reagent, preferably 1-propanephosphonic acid cyclic anhydride ($T_3P$). Alternatively, the reagent 1-[3-(dimethylamino)propyl]-3-ethylcarbodiimide (EDC) in a polar solvent, such as dimethylformamide, may be employed. If desired, or appropriate, an acyl transfer catalyst, such as 1-hydroxybenzotriazole (HOBT) or 1-hydroxy-7-aza-benzotriazole (HABT), may be added. Treatment of amide (I) with a hydride reducing agent, preferably lithium aluminum hydride (LAH), in a reaction-inert solvent, preferably THF, at elevated temperature, affords the corresponding aryl methylamine derivative (Ic).

Alternatively, the compounds of formula (I) wherein $R^1$ is hydrogen and $R^2$ represents $-COR^5$, $-CONR^3R^4$, $-CH_2NR^3R^4$, and the like, are conveniently prepared according to the exemplary method shown in Scheme 4.

Scheme 4

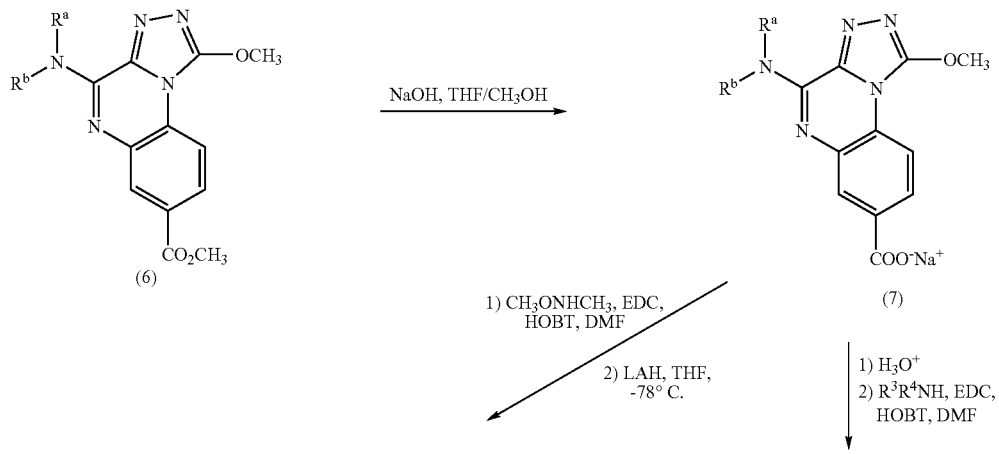

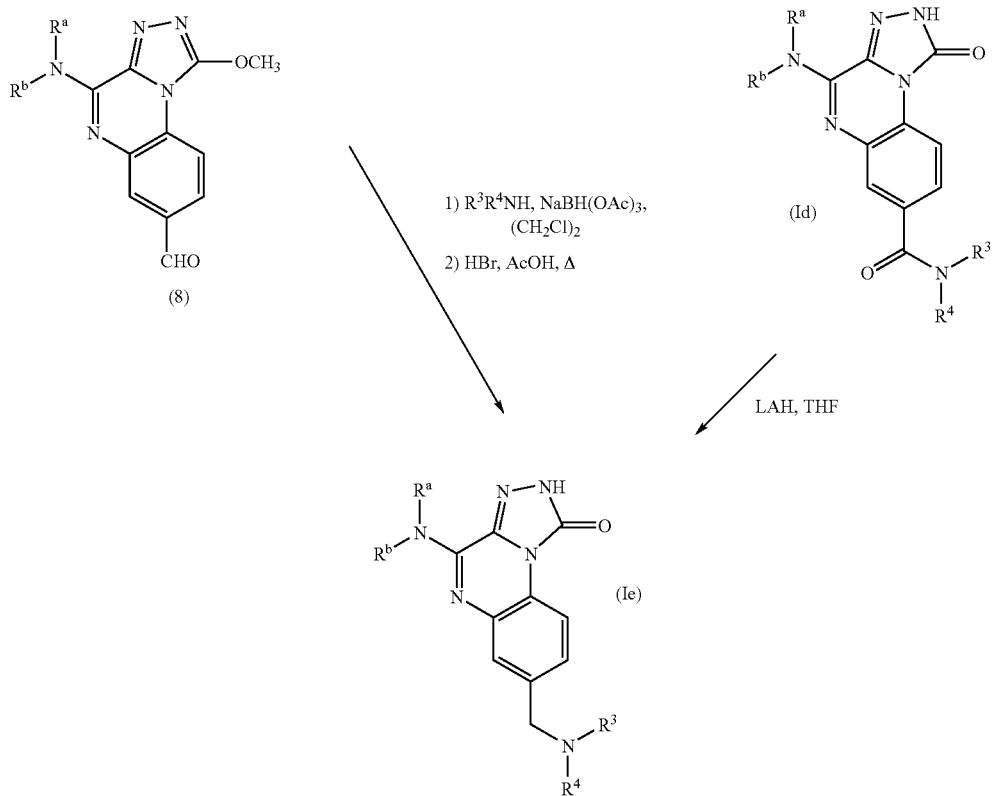

In Scheme 4, a 4-amino-7-carboxymethyl-1-methoxyquinoxaline derivative (6) is saponified, typically with base, for example, sodium hydroxide, to provide the corresponding sodium salt (7). The saponification is conveniently effected in a methano/THF mixture. Treatment of the carboxylate salt with aqueous acid generates the free acid, and hydrolyzes the imidate functionality to afford a triazolone carboxylic acid. The acid may then be converted into the corresponding amide (Id), and/or amine (Ie) according to the methods described hereinabove in Scheme 3. Alternatively, the reduction of amide (Id) may be effected with sodium borohydride and a Lewis Acid additive, preferably boron trifluoride etherate, in a reaction-inert solvent, such as THF.

Alternatively, (7) may be converted into the corresponding N-methyl-N-methoxyamide with a coupling reagent, preferably EDC in the presence of HOBT in a polar, aprotic solvent, such as DMF. The resulting adduct is then treated with a hydride reducing agent, preferably LAH, in a reaction-inert solvent, typically THF, at below ambient temperature, generally at −78° C., to form aldehyde (8). Subsequently, the amine functionality may be appended by reductive amination whereby aldehyde (8) is admixed with an appropriately-substituted amine $R^3R^4NH$ in the presence of a reducing agent, preferably sodium triacetoxyborohydride, in a reaction-inert solvent, preferably 1,2-dichloroethane. Subsequent exposure to HBr/AcOH at elevated temperature removes the imidate ether of (8) to afford (Ie).

Alternatively, the compounds of formula (Ib) depicted in Scheme 4, may also be conveniently prepared according to the exemplary method shown in Scheme 5.

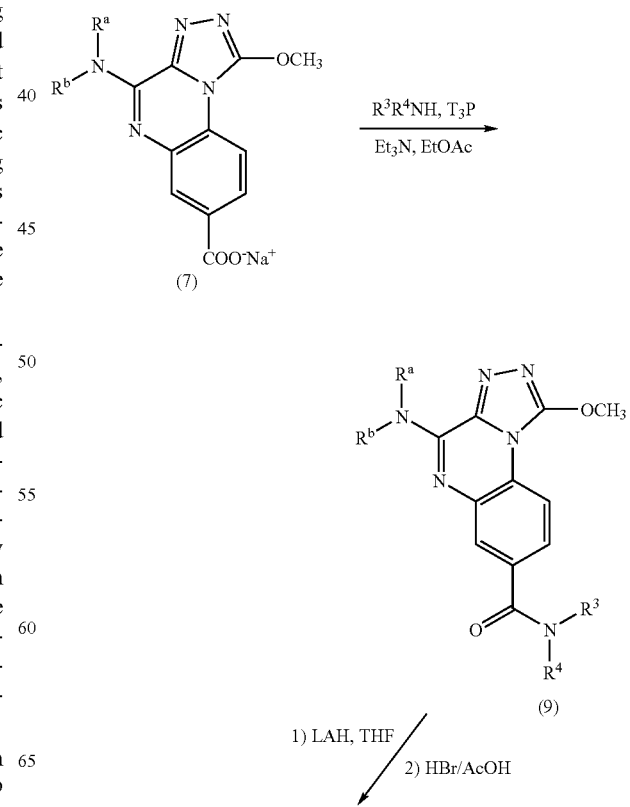

-continued

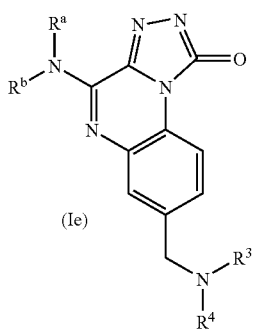

(Ie)

In Scheme 5, the quinoxaline sodium salt (7) is treated with an appropriately-substituted amine $R^3R^4NH$ in an organic solvent, such as ethyl acetate, in the presence of a coupling reagent, preferably $T_3P$, and an organic base, such as triethylamine to afford amide (9). Treatment of (9) with a hydride reducing agent, preferably LAH, in a reaction-inert solvent, preferably THF, affords the intermediate amine, which is then treated with HBr/AcOH at elevated temperature to cleave the imidate ether and provide (Ie).

PREPARATIVE EXPERIMENTAL

Unless otherwise noted, all reagents employed were obtained commercially. Unless otherwise noted, the following experimental abbreviations have the meanings indicated:
AcOH—acetic acid
DMF—dimethylformamide
DMSO—dimethylsulfoxide
EDC 1-[3-(dimethy/amino)propyl]-3-ethylcarbodiimide hydrochloride
equiv.—equivalent(s)
EtOAc—ethyl acetate
EtOH—ethanol
HPLC—high performance liquid chromatography
HOBT—1-hydroxybenzotriazole
hr(s).—hour(s)
MeOH—methanol
min(s).—minute(s)
IPE—diisopropyl ether
IPA—isopropanol
LAH—lithium aluminum hydride
mL—milliliter(s)
mmol—millimole(s)
MS—mass spectrometry
NMR—nuclear magnetic resonance
THF—tetrahydrofuran
TLC—thin layer chromatography
TF—trifluoroacetic acid The amine starting materials of formula $R^aR^bNH$ may be prepared according to conventional synthetic methods, or obtained from commercial sources. General procedures for preparing 2-alkylaminobenzimidazoles are disclosed in K. C. Nicolaou, et al., Bioorg. Med. Chem., 6, 1185–1208 (1998). Exemplary procedures (Methods A and B) for preparing certain heterocyclic ethane- and propane-diamine derivatives are set forth hereinbelow in Preparations 1–32.

The various 4-chloro-1-methoxy-[1,2,4]triazolo[4,3-a]quinoxaline starting materials were prepared according to the method of R. Sarges, et al., J. Med. Chem., 33, 2240 (1990).

Preparation 1

Method A $N^1$-(7-Trifluoromethyl-quinolin-4-yl)-ethane-1,2-diamine

A mixture of 120 mg of 4-chloro-7-trifluoromethylquinoline and 250 mg of tert-butyl-N-(2-aminoethyl)carbamate was heated to 125° C. for two hrs. The mixture was cooled to room temperature and partitioned between 10% IPA/chloroform and saturated sodium bicarbonate. The aqueous layer was back extracted with 10% IPA/chloroform and the organic layers were dried over sodium sulfate, filtered and concentrated. The residue was dissolved in EtOAc and washed with water, and the organic layer was dried over sodium sulfate, filtered, and concentrated. The product was dissolved in MeOH (0.5 mL) and stirred with five equiv. of 4.0 M HCl in dioxane for 18 hrs. The reaction mixture was concentrated and the residue was recrystallized from MeOH to afford the title compound. MS $(M+H)^+=256.1$.

The following 1,2- and 1,3-diamines were prepared in a manner analogous to that described in Preparation 1 using appropriate starting materials.

| Prep'n. | Name | MS (M + H)+ |
| --- | --- | --- |
| 2 | $N^1$-(4-trifluoromethyl-pyrimidin-2-yl)-ethane-1,2-diamine | 205.1 |
| 3 | $N^1$-benzooxazol-2-yl-ethane-1,2-diamine | 176.1 |
| 4 | $N^1$-benzothiazol-2-yl-ethane-1,2-diamine | 194.1 |
| 5 | $N^1$-(5-trifluoromethyl-pyridin-2-yl)-propane-1,3-diamine | 220.1 |
| 6 | $N^1$-(4-trifluoromethyl-pyridin-2-yl)-propane-1,3-diamine | 220.2 |
| 7 | $N^1$-(8-trifluoromethyl-quinolin-4-yl)-ethane-1,2-diamine | 254.1 |
| 8 | $N^1$-(2-trifluoromethyl-quinolin-4-yl)-ethane-1,2-diamine | 254.1 |
| 9 | $N^1$-(6-trifluoromethyl-quinolin-4-yl)-ethane-1,2-diamine | 254.1 |
| 10 | $N^1$-(6-chloro-benzothiazol-2-yl)-ethane-1,2-diamine | 226.0 |
| 11 | $N^1$-(6-methoxy-benzothiazol-2-yl)-ethane-1,2-diamine | 222.1 |
| 12 | 2-(2-amino-ethylamino)-isonicotinic acid | 180.2 |

Preparation 13

Method B $N^1$-Methyl-$N^2$-pyrimidin-2-yl-ethane-1,2-diamine

A solution of 100 mg of N-methylethylenediamine, 245 mg of 2-chloro-5-trifluoromethylpyridine and 261 mg of diisopropylethylamine in toluene was heated at 110° C. for 18 hrs. The reaction mixture was concentrated, poured into water, and extracted with 10% IPA/chloroform. The organic extracts were dried over sodium sulfate, filtered, and concentrated to provide the desired title compound contaminated with <3% of the bis-substituted dimer. MS $(M+H)^+=220.2$.

The following 1,2-diamines were prepared in a manner analogous to that described in Preparation 13 using appropriate starting materials.

| Prep'n. | Name | MS (M + H)+ |
|---|---|---|
| 14 | $N^1$-(1H-benzoimidazol-2-yl)-ethane-1,2-diamine | 177.2 |
| 15 | $N^1$-(4-trifluoromethyl-pyridin-2-yl)-ethane-1,2-diamine | 206.4 |
| 16 | $N^1$-(pyridin-2-yl)-ethane-1,2-diamine | 138.1 |
| 17 | $N^1$-(quinolin-2-yl)-ethane-1,2-diamine | 206.4 |
| 18 | $N^1$-(pyridin-4-yl)-ethane-1,2-diamine | 137.9 |
| 19 | $N^1$-pyrimidin-2-yl-ethane-1,2-diamine | 139.1 |

Preparation 20

$N^1$-(Pyridin-3-yl)-ethane-1,2-diamine

A mixture of 1.32 g of ethylenediamine, 250 mg of 3-chloropyridine, and 740 mg of potassium tert-butoxide was heated at 118° C. in a sealed tube for 18 hrs. The reaction was cooled to room temperature, diluted with water and extracted with chloroform. The organic extracts were dried over sodium sulfate, filtered, and concentrated to give the title product as a red oil. MS $(M+H)^+$=137.9.

Preparation 21

$N^1$-Triazin-2-yl-ethane-1,2-diamine

Step A

A solution of 434 mg of tert-butyl-N-(2-aminoethyl) carbamate and 576 mg of sodium carbonate in DMF (9.0 mL) at 0° C. was stirred as a solution of 500 mg of cyanuric chloride in DMF (2.0 mL) was added. The reaction mixture was stirred at 0° C. for two hrs., at room temperature for three hrs., and then poured into water to form a white suspension. The solid was collected and the filtrate was extracted with EtOAc and concentrated to provide a crude sample. The solids were combined and separated by silica gel chromatography to give the mono-ethylamine adduct.

Step B

The product from Step A was dissolved in absolute EtOH (7.6 mL) and 50 mg of 10% Pd/C was added, followed by 480 mg of ammonium formate. The mixture was heated at reflux for one hr., the solids were removed by filtration through diatomaceous earth, and washed with hot EtOH. The filtrate was concentrated to give a white solid.

Step C

The product of Step B was dissolved in MeOH (1.9 mL) and stirred together with 5 equiv. of 4.0 M HCl in dioxane for two hrs. The white solid that formed was collected and dried to give the title compound as the hydrochloride salt. MS $(M+H)^+$=140.1.

Preparation 22

$N^1$-(1-Methyl-piperidin-4-yl)-ethane-1,2-diamine

Step A

To a solution of 220 mg of N-methyl-4-piperidone and 283 mg of tert-butyl-(2-amino-ethyl)carbamate in methylene chloride (6.0 mL) was added 563 mg of sodium triacetoxyborohydride and 212 mg of acetic acid. This mixture was stirred at room temperature for 12 days and quenched by the addition of 1 N sodium hydroxide, followed by extraction with methylene chloride (4×). The extracts were dried over sodium sulfate, filtered, and concentrated to give a yellow, oily product.

Step B

The product of Step A was dissolved in MeOH (3.0 mL) and stirred with 5 equivalents of 4.0 M HCl in dioxane (3.0 mL) for 18 hrs. The reaction mixture was concentrated to give the title compound as a light yellow solid. MS $(M+H)^+$=158.1.

Preparation 23

2-Benzothiazol-2-yl-ethylamine

A solution of 50 mg of 3-aminopropionitrile and 596 mg of 2-aminothiophenol in EtOH (15 mL) was heated at reflux for six hrs. After cooling the solution to room temperature, the reaction was concentrated and the residue was purified by silica gel chromatography to afford the title compound as a red oil. MS $(M+H)^+$=179.1.

Preparation 24

$N^1$-(6-Methyl-5,6,7,8-tetrahydro-[1,6]naphthyridin-2-yl)-ethane-1,2-diamine

Step A

A solution of 250 mg of 2-chloro-5,6,7,8-tetrahydro-[1,6]naphthyridine (U.S. Pat. No. 6,169,093) in methylene chloride (6.1 mL) was treated with 0.148 mL of a 37% formalin solution, followed by 0.388 g of sodium triacetoxyborohydride. The reaction mixture was stirred at room temperature for 60 hrs. and quenched by the addition of 2N sodium hydroxide (6 mL). After stirring for 1 hr., the mixture was diluted with water and extracted with methylene chloride (2×). The organic layers were dried over sodium sulfate, filtered, and concentrated. Purification of the residue using silica gel chromatography provided N-methylchloronaphthyridine.

Step B

The product from Step A was dissolved in 10 equiv. of ethylenediamine and heated at 138° C. in a sealed tube for 18 hrs. The excess ethylenediamine was removed by distillation to provide the title compound as a brown oil. MS $(M+H)^+$=207.0.

Preparation 25

2-(Pyridin-2-yloxy)-ethylamine

A mixture of 500 mg of 2-aminoethanol and 328 mg of 60% sodium hydride-mineral oil dispersion in dioxane (27 mL) was heated to reflux for 30 min. After cooling to room temperature, 930 mg of 2-chloropyridine was added and the mixture was warmed to reflux and maintained at this temperature for 18 hrs. The reaction mixture was concentrated, diluted with water, and extracted with chloroform (3×). The organic extracts were washed with saturated brine, dried over sodium sulfate, filtered, concentrated, and the residue was purified by silica gel chromatography to give the title product as a yellow oily material. MS $(M+H)^+$=138.9.

Preparation 26

2-Amino-1-(7,8-dihydro-5H-[1,6]naphthyridin-6-yl)-ethanone

Step A

A solution of 90 mg of 2-chloro-5,6,7,8-tetrahydro-[1,6]naphthyridine hydrochloride (U.S. Pat. No. 6,169,093), 0.134 g of N-carbobenzyloxyglycine, 0.130 g of triethylamine, and 0.087 g of 1-hydroxy-7-azabenzotriazole in DMF (2.7 mL) at 0° C. was stirred as 0.123 g (0.640 mmol) of EDC was added. After two hrs., the reaction mixture was poured into 4% magnesium sulfate solution, and the resulting solution was extracted with EtOAc and then methylene chloride. The organic extracts were dried over sodium sulfate, filtered, and concentrated to give an oil that solidified upon standing. Trituration with MeOH and collection of the solids provided the desired amide intermediate.

Step B

To a solution of 93 mg (0.260 mmol) of the product from Step A in a 3:2 THF/MeOH mixture (5 mL) was added 100 mg of 10% Pd/C and 300 mg of cyclohexene. This mixture was heated to reflux for 16 hrs., cooled to room temperature, and filtered through a short pad of diatomaceous earth. The solids were washed with methylene chloride, and the filtrate was concentrated to provide the title compound. MS (M+H)$^+$=192.1.

Preparation 27

2-(4-Methyl-piperazin-1-yl)-ethylamine

Step A

A solution of 0.90 g of 4-methylpiperazine, 0.830 g of chlorcacetonitrile, and 6.0 g of potassium carbonate in acetonitrile (9 mL) was stirred for 72 hrs. The reaction mixture was filtered and the filtrate was concentrated to provide a yellow solid.

Step B

The product from Step A was dissolved in a 1:1 mixture of ether/THF and was added to a suspension of 330 mg of LAH in ether (10 mL) at 0° C. The reaction was stirred at room temperature for 24 hrs., cooled to 0° C., and 5 mL of a solution of 6.0 N sodium hydroxide was added with stirring for 20 min. The solids were removed by filtration, and the filtrate was concentrated, dissolved in ether, dried over sodium sulfate, filtered, and concentrated to give the title compound as a light yellow oil. MS (M+H)$^+$=144.1.

Preparation 28

2-(3,4-Dihydro-1H-isoquinolin-2-yl)-ethylamine

Step A

A solution of 273 mg of methanesulfonic acid 2-benzyloxycarbonylamino-ethyl ester, 133 mg of 1,2,3,4-tetrahydroisoquinoline and 212 mg of sodium carbonate in DMF (3.0 mL) was heated to 90° C. for six hrs. The reaction mixture was cooled to room temperature, diluted with EtOAc, washed with water and saturated brine, dried over sodium sulfate, filtered, and concentrated. The residue was purified by silica gel chromatography to afford a yellow, oily product.

Step B

To a solution of 255 mg of the product from Step A in MeOH (3.0 mL) was added 99 mg of acetic acid, 102 mg of 10% Pd/C and 518 mg of ammonium formate. The mixture was refluxed for two hrs., cooled to room temperature, and filtered through a pad of diatomaceous earth. The filtrate was concentrated to give the title compound as a yellow oil. MS (M+H)$^+$=177.2.

The following 1,2-diamines were prepared in a manner analogous to that described in Preparation 28 using appropriate starting materials.

| Prep'n. | Name | MS (M + H)$^+$ |
|---|---|---|
| 29 | N$^1$-Methyl-N$^2$-pyridin-2-ylmethyl-ethane-1,2-diamine | 164.9 |
| 30 | 2-(6,7-dimethoxy-3,4-dihydro-1H-isoquinolin-2-yl)-ethylamine | 237.2 |

Preparation 31

N$^1$-(4-Morpholin-4-ylmethyl-pyridin-2-yl)-ethane-1,2-diamine

Step A

A solution of 315 mg of 2-chloroisonicotinic acid and 209 mg of morpholine in EtOAc (4.0 mL) was stirred as 1.27 g of a 50% solution of 1-propanephosphonic acid cyclic anhydride was added. This mixture was stirred at room temperature for six hrs. and another 1.27 g of the anhydride was added followed by stirring for another 18 hrs. The reaction was poured into saturated sodium bicarbonate solution and extracted with EtOAc (3×). The organic layers were dried over sodium sulfate, filtered, and concentrated to provide the morpholine amide.

Step B

A mixture of 220 mg of the product from Step A was heated with 467 mg of tert-butyl-N-(2-aminoethyl)carbamate at 125° C. for 18 hrs. Diisopropylethylamine (371 mg) was added and heating was continued for 48 hrs. The reaction mixture was cooled to room temperature and purified by silica gel chromatography to provide the desired intermediate.

Step C

A solution of 155 mg of the product from Step B in THF (1.5 mL) and 0.66 mL of a 1.0 M solution of LAH in THF was heated at reflux for five hrs. The reaction was cooled to 0° C. and quenched by the sequential addition of 25 µL of water, 25 µL of 3.0 N sodium hydroxide, 75 µL of water, and solid sodium sulfate. The solids were removed by filtration and the filtrate was concentrated to leave a residue that was purified by silica gel chromatography to provide an oily product.

Step D

A solution of 50 mg of the product from Step C was dissolved in 10 equiv. of a 4.0 M solution of HCl in dioxane. This mixture was stirred for 90 min. and then concentrated to give the title compound as the hydrochloride salt. MS (M+H)$^+$=237.3.

The following 1,2-diamine was prepared in a manner analogous to that described in Preparation 31 using appropriate starting materials.

| Prep'n. | Name | MS (M + H)+ |
|---|---|---|
| 32 | N¹-[4-(4-Methyl-piperazin-1-ylmethyl)-pyridin-2-yl]-ethane-1,2-diamine | 250.3 |

Exemplary procedures for preparing the compounds of formula (I) according to Schemes 1–5 hereinabove are set forth in the following Examples.

EXAMPLE 1

8-Fluoro-4-phenethylamino-2H-[1,2,4]triazolo[4,3-a]quinoxaline-1-one

To a solution of 0.10 g of 4-chloro-8-fluoro-1-methoxy-[1,2,4]triazolo[4,3-a]quinoxaline in DMF (1.3 mL) was added 0.144 g of 2-phenylethylamine. This solution was stirred at room temperature for 72 hrs., and then poured into cold water. The solid was dissolved in methylene chloride and washed with saturated brine, dried over sodium sulfate, filtered, and concentrated to provide 0.102 g of a light yellow solid. The solid was dissolved in a 1:1.5 mixture of 48% HBr/AcOH and was refluxed for two hrs. The reaction was concentrated and the residue was recrystallized from MeOH to provide the hydrobromide salt of the title compound as a yellow solid. MS (M+H)$^{30}$=322.1.

The following compounds of formula (I) were prepared in a manner analogous to that described in Example 1 using appropriate starting materials.

| Example | Name | MS (M + H)+ or (M − H)− |
|---|---|---|
| 2 | 8-fluoro-4-(2-naphthalen-1-yl-ethylamino)-2H-[1,2,4]triazolo[4,3-a]quinoxalin-1-one | 372.0 (−) |
| 3 | 8-fluoro-4-cyclohexylamino-2H-[1,2,4]triazolo[4,3-a]quinoxalin-1-one | 300.1 (−) |
| 4 | 4-[2-(4-chloro-phenyl)-ethylamino]-8-fluoro-2H-[1,2,4]triazolo[4,3-a]quinoxalin-1-one | 356.0 (−) |
| 5 | 4-[2-(4-fluoro-phenyl)-ethylamino]-8-fluoro-2H-[1,2,4]triazolo[4,3-a]quinoxalin-1-one | 340.0 (−) |
| 6 | 4-[2-(4-methyl-phenyl)-ethylamino]-8-fluoro-2H-[1,2,4]triazolo[4,3-a]quinoxalin-1-one | 336.0 (−) |
| 7 | 8-fluoro-4-(2-pyridin-4-yl-ethylamino)-2H-[1,2,4]triazolo[4,3-a]quinoxalin-1-one | 323.0 (−) |
| 8 | 8-fluoro-4-(2-morpholin-4-yl-ethylamino)-2H-[1,2,4]triazolo[4,3-a]quinoxalin-1-one | 331.1 (−) |
| 9 | 8-fluoro-4-(4-phenyl-butylamino)-2H-[1,2,4]triazolo[4,3-a]quinoxalin-1-one | 350.0 (−) |
| 10 | 8-fluoro-4-(4-phenyl-propylamino)-2H-[1,2,4]triazolo[4,3-a]quinoxalin-1-one | 336.0 (−) |
| 11 | 8-fluoro-4-(2-pyridin-2-yl-ethylamino)-2H-[1,2,4]triazolo[4,3-a]quinoxalin-1-one | 323.0 (−) |
| 12 | 8-fluoro-4-[2-(1H-indol-3-yl)-ethylamino]-2H-[1,2,4]triazolo[4,3-a]quinoxalin-1-one | 361.0 (−) |
| 13 | 4-[2-(1H-benzoimidazol-2-yl)-ethylamino]-8-fluoro-2H-[1,2,4]triazolo[4,3-a]quinoxalin-1-one | 362.0 (−) |
| 14 | 4-[2-(1H-benzoimidazol-2-yl)-propylamino]-8-fluoro-2H-[1,2,4]triazolo[4,3-a]quinoxalin-1-one | 376.0 (−) |
| 15 | 4-[2-(1H-benzoimidazol-2-yl)-methylamino]-8-fluoro-2H-[1,2,4]triazolo[4,3-a]quinoxalin-1-one | 347.8 (−) |
| 16 | 8-fluoro-4-{methyl-[2-(5-trifluoromethyl-pyridin-2-ylamino)-ethyl]-amino}-2H-[1,2,4]triazolo[4,3-a]quinoxalin-1-one | 419.9 (−) |
| 17 | 4-[2-(1H-benzoimidazol-2-yl)-butylamino]-8-fluoro-2H-[1,2,4]triazolo[4,3-a]quinoxalin-1-one | 390.0 (−) |
| 18 | 8-fluoro-4-[2-(7-trifluoromethyl-quinolin-4-ylamino)-ethylamino]-2H-[1,2,4]triazolo[4,3-a]quinoxalin-1-one | 455.8 (−) |
| 19 | 4-[2-(1H-benzoimidazol-2-ylamino)-ethylamino]-8-fluoro-2H-[1,2,4]triazolo[4,3-a]quinoxalin-1-one | 377.0 (−) |
| 20 | 4-[2-(benzooxazol-2-ylamino)-ethylamino]-8-fluoro-2H-[1,2,4]triazolo[4,3-a]quinoxalin-1-one | 377.9 (−) |
| 21 | 4-[2-(1H-benzothiazol-2-ylamino)-ethylamino]-8-fluoro-2H-[1,2,4]triazolo[4,3-a]quinoxalin-1-one | 393.9 (−) |
| 22 | 8-fluoro-4-[2-(4-trifluoromethyl-pyrimidin-2-ylamino)-ethylamino]-2H-[1,2,4]triazolo[4,3-a]quinoxalin-1-one | 408.9 (+) |
| 23 | N-[2-(8-fluoro-1-oxo-1,2,-dihydro[1,2,4]triazolo[4,3-a]quinoxalin-4-ylamino)-ethyl]-guanidine | 303.0 (+) |
| 24 | 8-fluoro-4-[2-(5-trifluoromethyl-1H-benzoimidazol-2-yl)-ethylamino]-2H-[1,2,4]triazolo[4,3-a]quinoxalin-1-one | 429.9 (−) |
| 25 | 8-fluoro-4-[2-(5-trifluoromethyl-1H-benzoimidazol-2-yl)-butylamino]-2H-[1,2,4]triazolo[4,3-a]quinoxalin-1-one | 457.9 (−) |
| 26 | 8-fluoro-4-[2-(4-trifluoromethyl-pyridin-2-ylamino)-propylamino]-2H-[1,2,4]triazolo[4,3-a]quinoxalin-1-one | 421.9 (+) |
| 27 | 8-fluoro-4-[2-(4-methyl-piperazin-1-yl)-ethylamino]-2H-[1,2,4]triazolo[4,3-a]quinoxalin-1-one | 344.0 (+) |
| 28 | 8-fluoro-4-[2-(8-trifluoromethyl-quinolin-4-ylamino)-ethylamino]-2H-[1,2,4]triazolo[4,3-a]quinoxalin-1-one | 457.4 (+) |
| 29 | 8-fluoro-4-[2-(6-trifluoromethyl-quinolin-4-ylamino)-ethylamino]-2H-[1,2,4]triazolo[4,3-a]quinoxalin-1-one | 455.8 (−) |
| 30 | 8-fluoro-4-[2-(2-trifluoromethyl-quinolin-4-ylamino)-ethylamino]-2H-[1,2,4]triazolo[4,3-a]quinoxalin-1-one | 457.9 (+) |
| 31 | 4-[2-(6-chloro-benzothiazol-2-ylamino)-ethylamino]-8-fluoro-2H-[1,2,4]triazolo[4,3-a]quinoxalin-1-one | 427.8 (−) |
| 32 | 4-[2-(6-methoxy-benzothiazol-2-ylamino)-ethylamino]-8-fluoro-2H-[1,2,4]triazolo[4,3-a]quinoxalin-1-one | 423.9 (−) |
| 33 | 8-fluoro-4-[2-(1-methyl-piperidin-4-ylamino)-ethylamino]-2H-[1,2,4]triazolo[4,3-a]quinoxalin-1-one | 358.3 (−) |
| 34 | 8-fluoro-4-[2-(pyridin-2-ylamino)-ethylamino]-2H-[1,2,4]triazolo[4,3-a]quinoxalin-1-one | 338.0 (−) |
| 35 | 8-fluoro-4-[2-(quinolin-2-ylamino)-ethylamino]-2H-[1,2,4]triazolo[4,3-a]quinoxalin-1-one | 387.9 (−) |
| 36 | 4-(2-benzothiazol-2-yl-ethylamino)-8-fluoro-2H-[1,2,4]triazolo[4,3-a]quinoxalin-1-one | 379.2 (−) |
| 37 | 8-fluoro-4-[2-(pyridin-4-ylamino)-ethylamino]-2H-[1,2,4]triazolo[4,3-a]quinoxalin-1-one | 338.3 (−) |
| 38 | 4-[2-(3,4-dihydro-1H-isoquinolin-2-yl)-ethylamino]-8-fluoro-2H-[1,2,4]triazolo[4,3-a]quinoxalin-1-one | 377.3 (−) |
| 39 | 4-[2-(7,8-dihydro-5H-[1,6]naphthyridin-6-yl)-2-oxo-ethylamino]-8-fluoro-2H-[1,2,4]triazolo[4,3-a]quinoxalin-1-one | 392.1 (−) |
| 40 | 8-fluoro-4-[2-(6-methyl-5,6,7,8-tetrahydro-[1,6]naphthyridin-2-ylamino)-ethylamino]-2H-[1,2,4]triazolo[4,3-a]quinoxalin-1-one | 407.3 (−) |

| Example | Name | MS (M + H)+ or (M − H)− |
|---|---|---|
| 41 | 8-fluoro-4-[2-(4-morpholin-4-ylmethyl-pyridin-2-ylamino)-ethylamino]-2H-[1,2,4]triazolo[4,3-a]quinoxalin-1-one | 437.2 (−) |
| 42 | 2-[2-(8-fluoro-1-oxo-1,2-dihydro[1,2,4]triazolo[4,3-a]quinoxalin-4-ylamino-ethylamino]-isonicotinic acid | 384.3 (+) |
| 43 | 4-[2-(6,7-dimethoxy-3,4-dihydro-1H-isoquinolin-2-yl)-ethylamino]-8-fluoro-2H-[1,2,4]triazolo[4,3-a]quinoxalin-1-one | 437.3 (−) |
| 44 | 8-fluoro-4-[2-(methyl-pyridin-4-ylmethyl-amino)-ethylamino]-2H-[1,2,4]triazolo[4,3-a]quinoxalin-1-one | 366.3 (−) |
| 45 | 8-fluoro-4-(piperidin-4-ylamino)-2H-[1,2,4]triazolo[4,3-a]quinoxalin-1-one | 301.0 (−) |
| 46 | 8-bromo-4-isopropylamino-2H-[1,2,4]triazolo[4,3-a]quinoxalin-1-one | 324.2 (+) |
| 47 | 4-[2-(benzothiazol-2-ylamino)-ethylamino]-8-bromo-2H-[1,2,4]triazolo[4,3-a]quinoxalin-1-one | 456.0 (+) |
| 48 | 8-chloro-4-isopropylamino-2H-[1,2,4]triazolo[4,3-a]quinoxaline-1-one | 278.0 (+) |

EXAMPLE 49

4-Benzylamino-8-fluoro-2H-[1,2,4]triazolo[4,3-a]quinoxaline-1-one

To a solution of 500 mg of 4-chloro-8-fluoro-1-methoxy-[1,2,4]triazolo[4,3-a]quinoxaline in DMF (6.0 mL) was added 637 mg of benzylamine. This solution was stirred at room temperature for 18 hrs. and then diluted with EtOAc and washed with water and saturated lithium chloride. The extracts were dried over sodium sulfate, filtered, and concentrated and the residue was separated by silica gel chromatography to give a yellow solid. This material was dissolved in a 1:1.5 mixture of 48% HBr/AcOH, and refluxed for 12 hrs. The reaction mixture was concentrated and the residue was recrystallized from MeOH to afford the title compound as a yellow solid. MS (M+H)+=310.0.

EXAMPLE 50

8-Bromo-4-[2-(1H-indol-3-yl)-ethylaminol-2H-[1,2,4]triazolor[4,3-a]quinoxaline-1-one To a solution of 50 mg of 4-chloro-8-bromo-1-methoxy-[1,2,4]triazolo[4,3-a]quinoxaline in DMF (1.0 mL) was added 51 mg of tryptamine. This solution was stirred at room temperature for 18 hrs., and then diluted with EtOAc and washed with water and saturated brine. The extracts were dried over sodium sulfate, filtered, and concentrated to provide a solid that was dissolved in a 1:1.5 mixture of 48% HBr/AcOH and was refluxed for two hrs. The reaction was concentrated and the residue was separated by silica gel chromatography to give the title compound as a yellow solid. MS (M+H)+=423.3.

The following compound of formula (I) was prepared in a manner analogous to that described in Example 50 using appropriate starting materials, except the deprotection step was effected with 4.0 M HCl in dioxane.

| Example | Name | MS (M + H)− |
|---|---|---|
| 51 | 6-Fluoro-4-[2-(pyridin-2-yloxy)-ethylamino]-2H-[1,2,4]triazolo[4,3-a]quinoxaline-1-one | 339.2 |

EXAMPLE 52

8–Chloro-4-phenethylamino-2H-[1,2,4]triazolo[4,3-a]quinoxazline-1-one

To a solution of 100 mg of 4,8-dichloro-1-methoxy[1,2,4]triazolo[4,3-a]quinoxaline in DMF (2.0 mL) was added 112 mg of 2-phenethylamine. This solution was stirred at room temperature for 18 hrs., and then diluted with EtOAc and washed with water and saturated lithium chloride. The extracts were dried over sodium sulfate, filtered, and concentrated to provide a residue that was separated by silica gel chromatography to give a yellow solid. This solid was dissolved in a 1:1.5 mixture of 48% HBr/AcOH and was refluxed for 12 hrs. The reaction was concentrated and the residue was separated by silica gel chromatography to give the title compound as a white solid. MS (M+H)+=340.0.

EXAMPLE 53

4-(2-Pyridin-4-yl-ethylamino)-2H-[1,2,4]triazolo[4,3-a]quinoxazline-1-one

A solution of 70 mg of 4-chloro-1-methoxy[1,2,4]triazolo[4,3-a]quinoxaline, 47 mg of 4-(2-aminoethyl)pyridine, and 49 mg of sodium bicarbonate in DMF (3.0 mL) was stirred at 50° C. for seven hrs. After pouring the reaction mixture into water, it was extracted with EtOAc, and the organic layer was washed with saturated brine, dried over sodium sulfate, filtered, and concentrated. The residue was triturated with 1% MeOH/methylene chloride, and the bright orange solid was collected and dried. This solid was dissolved in a 1:1.5 mixture of 48% HBr/AcOH, and stirred at room temperature for 90 min. The reaction mixture was concentrated and the residue was triturated to provide the title compound as a solid. MS (M+H)+=307.0.

The following compounds of formula (I) were prepared in a manner analogous to that described in Example 53 using appropriate starting materials.

| Example | Name | MS (M + H)+ |
|---|---|---|
| 54 | 4-[2-(Benzothiazol-2-ylamino)-ethylamino]-2H-[1,2,4]triazolo[4,3-a]quinoxaline-1-one | 378.0 |
| 55 | 4-[2-(4-Trifluoromethyl-pyridin-2-ylamino)-ethylamino]-2H-[1,2,4]triazolo[4,3-a]quinoxaline-1-one | 390.0 |
| 56 | 4-[2-(Benzooxazol-2-ylamino)-ethylamino]-2H-[1,2,4]triazolo[4,3-a]quinoxaline-1-one | 360.0 |

EXAMPLE 57

8-Fluoro-4-(4-methoxy-benzylamino)-2H-[1,2,4]triazolo[4,3-a]quinoxalin-1-one To a solution of 1.0 g of 4-chloro-8-fluoro-1-methoxy[1,2,4]triazolo[4,3-a]quinoxaline in DMF (12.0 mL) was added 1.36 g of 4-methoxybenzylamine. This solution was stirred at room temperature for 18 hrs. and then diluted with EtOAc and washed with water and saturated lithium chloride. The extracts were dried over sodium sulfate, filtered, and concentrated and the residue was separated by silica gel chromatography to give a yellow solid. This solid was dissolved in MeOH (15 mL) and 160 mg of 10% Pd/C and 0.96 g of cyclohexene were added. This mixture was heated at reflux for 18 hrs., filtered through a pad of diatomaceous earth, and concentrated to provide an off-white solid. MS (M+H)$^+$ =340.0.

EXAMPLE 58

4-Isopropylamino-2H-[1,2,4]triazolo[4,3-a]quinoxaline-1-one

To a mixture of 40 mg of 8-bromo-4-isopropylamino-2H-[1,2,4]triazolo[4,3-a]quinoxalin-1-one and 40 mg of 10% Pd/C in a 1:1 mixture of MeOH/EtOH was added 81 mg of cyclohexene. This mixture was heated at reflux for 3.5 hrs. and then stirred at room temperature for 18 hrs. The reaction mixture was diluted with chloroform, filtered through a pad of diatomaceous earth, and concentrated. The residue was triturated with IPE to provide an orange solid. MS (M+H)$^+$ =244.0.

EXAMPLE 59

(8-Fluoro-1-oxo-1,2-dihydro-[1,2,4]triazolo[4,3-a]quinoxalin-4-ylamino)-acetic acid ethyl ester A solution of 152 mg of 4-chloro-8-fluoro-1-methoxy-[1,2,4]triazolo[4,3-a]quinoxaline, 127 mg of glycine ethyl ester hydrochloride, and 602 mg of triethylamine in DMF (4.0 mL) was stirred at room temperature for 41 hrs. The reaction mixture was concentrated, dissolved in 25% IPA/methylene chloride and washed with 50% saturated sodium bicarbonate, and then water. The organic emulsion was collected and concentrated to provide a yellow solid. A solution of this solid in trifluoroethanol (10 mL) was treated with 5 equiv. of 4.0 N HCl in dioxane for 15 min., and the mixture was concentrated. The residue was dissolved in 20% IPA/methylene chloride, and washed with 50% saturated sodium bicarbonate, and then water. The organic emulsion was collected and concentrated to provide a yellow solid which was triturated. The resulting off-white solid was collected, dried, washed with ether and dried to provide the title compound. MS (M+H)$^+$=306.0.

The following compounds of formula (I) were prepared in a manner analogous to that described in Example 59 using appropriate starting materials.

| Example | Name | MS (M + H)$^+$ or (M − H)$^−$ |
|---|---|---|
| 60 | 4-(8-(Fluoro-1-oxo-1,2-dihydro-[1,2,4]triazolo[4,3-a]quinoxaline-4-ylamino)-piperidine-1-carboxylic acid | 375.0 (+) |
| 61 | 8-Fluoro-4-[2-(1H-indol-3-yl)-1-methyl-ethylamino]-2H-[1,2,4]triazolo[4,3-a]quinoxaline-1-one | 377.0 (+) |
| 62 | 8-Fluoro-4-(tetrahydro-pyran-4-ylamino)-2H-[1,2,4]triazolo[4,3-a]quinoxaline-1-one | 302.0 (−) |

-continued

| Example | Name | MS (M + H)$^+$ or (M − H)$^−$ |
|---|---|---|
| 63 | 4-tert-Butylamino-8-fluoro-2H-[1,2,4]triazolo[4,3-a]quinoxalin-1-one | 274.0 (−) |
| 64 | 8-Fluoro-4-(2-methoxy-1-methyl-ethylamino)-2H-[1,2,4]triazolo[4,3-a]quinoxalin-1-one | 290.1 (−) |

EXAMPLE 65

4-[2-(Benzothiazol-2-ylamino)-ethylamino]-8-chloro-2H-[1,2,4]triazolo[4,3-a]quinoxalin-1-one To a solution of 100 mg of 4,8-dichloro-1-methoxy-[1,2,4]triazolo[4,3-a]quinoxaline and 109 mg of triethylamine in DMF (2.0 mL) was added 86 mg of N$^1$-benzothiazol-2-yl-ethane-1,2-diamine. This solution was stirred at room temperature for 18 hrs. and then diluted with 10% IPA/methylene chloride, and washed with water and brine. The extracts were dried over sodium sulfate, filtered, and concentrated. The residue was separated by silica gel chromatography to provide a yellow solid. This solid was dissolved in a 1:1.5 mixture of 48% HBr/AcOH and refluxed for 2 hrs. The reaction mixture was concentrated and the residue was triturated with IPE to provide the hydrobromide salt of the title compound as a yellow solid. MS (M+H)$^+$=412.2.

The following compound of formula (I) was prepared in a manner analogous to that described in Example 65 using appropriate starting materials.

| Example | Name | MS (M + H)$^+$ |
|---|---|---|
| 66 | 4-[2-(Benzooxazol-2-ylamino)-ethylamino]-8-chloro-2H-[1,2,4]triazolo[4,3-a]quinoxalin-1-one | 396.3 |

EXAMPLE 67

8-Fluoro-4-piperazin-1-yl-[1,2,4]triazolo[4,3-a]quinoxalin-1-one

A solution of 300 mg of 4-chloro-8-fluoro-1-methoxy-[1,2,4]triazolo[4,3-a]quinoxaline, 221 mg of tert-butyl-N-(piperazine)carbamate, and 360 mg of triethylamine in acetonitrile (4.0 mL) was stirred at room temperature. After 16 hrs., the solvent was removed, and the residue was separated by silica gel chromatography to give 280 mg of a yellow foam. The foam was dissolved in a 1:1.5 mixture of 48% HBr/AcOH, and the mixture was heated to reflux for 2 hrs. The reaction mixture was concentrated to give 97 mg of a yellow solid. MS (M−H)$^−$=287.1.

EXAMPLE 68

8-Fluoro-4-[4-(5-trifluoromethyl-pyridin-2-yl)-piperazin-1-yl]-2H-[1,2,4]triazolo[4,3-a]quinoxalin-1-one A solution of 40 mg of 8-fluoro-4-piperazin-1-yl-[1,2,4]triazolo[4,3-a]quinoxalin-1-one, 48 mg of 2-chloro-5-trifluoromethylpyridine, and 47 mg of sodium carbonate in n-butanol (1 mL) was heated to reflux for 24 hrs. The reaction mixture was cooled to room temperature, filtered through a plug of diatomaceous earth, and evaporated to dryness. The residue was separated by silica gel chromatography to provide a white solid. MS (M+H)$^+$=434.0.

EXAMPLE 69

8-Fluoro-4-[4-(5-cyano-pyridin-2-yl)-piperazin-1-yl]-2H-[1,2,4]triazolo[4,3-a]quinoxalin-1-one A solution of 40 mg of 8-fluoro-4-piperazin-1-yl-[1,2,4]triazolo[4,3-a]quinoxalin-1-one, 36.8 mg of 2-chloro-5-cyanopyridine, and 47 mg of sodium carbonate in n-butanol (1 mL) was heated to reflux for 24 hrs. The reaction mixture was cooled to room temperature, filtered through a plug of diatomaceous earth, and evaporated to dryness. The residue was separated by silica gel chromatography to provide a white solid. MS (M−H)$^-$=389.0.

EXAMPLE 70

4-(2-amino-ethylamino)-8-fluoro-2H-[1,2,4]triazolo[4,3-a]quinoxalin-1-one

Step A

A solution of 3.29 g of 4-chloro-8-fluoro-1-methoxy-[1,2,4]triazolo[4,3-a]quinoxaline, 2.30 g of tert-butyl-N-(2-aminoethyl)carbamate, and 3.96 g of triethylamine in acetonitrile (50 mL) was heated at 50° C. for nine hrs. The reaction mixture was cooled, the solvent was removed, the residue was dissolved in 10% IPA/chloroform, washed with saturated sodium bicarbonate, dried over sodium sulfate, filtered and concentrated. The residue was recrystallized from MeOH to provide a yellow solid.

Step B

The product from Step A (139 mg) was dissolved in a 1:1.5 mixture of 48% HBr/AcOH (4.6 mL) and heated at 100° C. for one hr. The reaction mixture was concentrated and the residue was recrystallized from MeOH to give the title compound as a light yellow solid. MS (M+H)$^+$=263.0.

EXAMPLE 71

8-Fluoro-4-[2-(5-trifluoromethyl-pyridin-2-Ylamino)-ethylamino]-2H-[1,2,4]triazolo[4,3-a]quinoxalin-1-one A solution of 259 mg of 4-(2-amino-ethylamino)-8-fluoro-2H-[1,2,4]triazolo[4,3-a]quinoxalin-1-one, 422 mg of 2-chloro-5-trifluoromethylpyridine and 411 mg of sodium carbonate in n-butanol (1 mL) was heated to reflux for 48 hrs. The reaction mixture was cooled to room temperature, filtered through diatomaceous earth, and the filtrate concentrated to give a solid residue. This was separated by silica gel chromatography to provide the title compound. MS (M+H)$^+$=407.9.

The following compounds of formula (I) were prepared in a manner analogous to that described in Example 71 using appropriate starting materials.

| Example | Name | MS (M − H)$^-$ |
|---|---|---|
| 72 | 8-Fluoro-4-[2-(cyano-pyridin-2-ylamino)-ethylamino]-2H-[1,2,4]triazolo[4,3-a]quinoxaline-1-one | 363.0 |
| 73 | 8-Fluoro-4-[2-(3-trifluoromethyl-pyridin-2-ylamino)-ethylamino]-2H-[1,2,4]triazolo[4,3-a]quinoxaline-1-one | 405.9 |
| 74 | 8-Fluoro-4-[2-(4-trifluoromethyl-pyridin-2-ylamino)-ethylamino]-2H-[1,2,4]triazolo[4,3-a]quinoxaline-1-one | 405.9 |
| 75 | 8-Fluoro-4-[2-(6-trifluoromethyl-pyridin-2-ylamino)-ethylamino]-2H-[1,2,4]triazolo[4,3-a]quinoxaline-1-one | 405.9 |

The following compound of formula (I) was prepared in a manner analogous to that described in Examples 70 and 71, using tert-butyl-(2-aminopropyl)carbamate.

| Example | Name | MS (M − H)$^-$ |
|---|---|---|
| 76 | 8-Fluoro-4-[2-(4-trifluoromethyl-pyridin-2-ylamino)-propylamino]-2H-[1,2,4]triazolo[4,3-a]quinoxaline-1-one | 419.9 |

EXAMPLE 77

Pyridine-2-carboxylic acid-[2-(8-fluoro-1-oxo-1,2-dihydro-[1,2,4]triazolo[4,3-a]quinoxalin-4-ylamino)-ethyl]-amide To a solution of 30 mg of 4-(2-amino-ethylamino)-8-fluoro-2H-[1,2,4]triazolo[4,3-a]quinoxalin-1-one in pyridine (0.38 mL) at 0° C. was added 20 mg of picolinyl chloride hydrochloride, and the mixture was stirred for 30 min. The mixture was concentrated and the residue was separated by silica gel chromatography to yield the title compound. MS (M−H)$^-$=366.2.

EXAMPLE 78

8-Fluoro-4-[2-(pyrimidin-2-ylamino)-ethylamino]-2H-[1,2,4]triazolo[4,3-a]quinoxalin-1-one A mixture of 50 mg of 4-(2-amino-ethylamino)-8-fluoro-2H-[1,2,4]triazolo[4,3-a]quinoxalin-1-one 13.5 mg of 2-chloropyrimidine, and 76 mg of diisopropylethylamine in DMSO (0.5 mL) was heated for 18 hrs. An additional 13.5 mg of 2-chloropyrimidine was added and heating was continued for another 18 hrs. The reaction was diluted with EtOAc, washed with water, and dried over sodium sulfate prior to concentration. The residue was separated by silica gel chromatography, and the isolated residue was recrystallized from MeOH to give the title compound. MS (M−H)$^-$=339.0.

EXAMPLE 79

[2-(8-Fluoro-1-oxo-1,2-dihydro-[1,2,4]triazolo[4,3-a]quinoxalin-4-ylamino)-ethyl[-carbamic acid, tert-butyl ester A solution of 500 mg of 4-chloro-8-fluoro-1-methoxy-[1,2,4]triazolo[4,3-a]quinoxaline, 350 mg of tert-butyl-N-(2-aminoethyl)carbamate, and 600 mg of triethylamine in acetonitrile (6.6 mL) was heated at reflux for 18 hrs. The reaction mixture was cooled, the solvent was removed, and the residue was separated by silica gel chromatography, followed by preparative TLC, to provide 260 mg of a yellow solid. MS $(M+H)^+=363.1$.

EXAMPLE 80

8-Fluoro-4-[1-(6-methyl-pyridine-2-carbonyl)-piperidin-4-ylamino]-2H-[1,2,4]triazolo[4,3-a]quinoxalin-1-one To a slurry of 98 mg of 8-fluoro-4-(piperidin-4-ylamino)-2H-[1,2,4]triazolo[4,3-a]quinoxalin-1-one, 33 mg of 6-methyl-picolinic acid, and 32 mg of HOBT in DMF (1.4 mL) was added 109 mg of triethylamine, followed by 47 mg of EDC and the mixture was stirred for 18 hrs. To this mixture was added 15 mg of 6-methyl-picolinic acid and 57 mg of benzotriazol-1-yl-oxy-trispyrrolidinophosphonium hexafluorophosphate, and stirring was continued for 30 min. The reaction mixture was diluted with water, and extracted with methylene chloride, and the organic extracts were washed with 50% saturated sodium bicarbonate and water, and then concentrated. The residue was separated using silica gel chromatography to provide a material that was dissolved in 10% MeOH/EtOAc, and washed with water. The organic extract was dried over sodium sulfate, filtered, and concentrated to provide the title compound as a white solid. MS $(M+H)^+=422.0$.

EXAMPLE 81

N-(8-Fluoro-1-oxo-1,2-dihydro-[1,2,4]triazolo[4,3-a]quinoxalin-4-yl)-acetamide

Step A

A solution of 496 mg of 4-chloro-8-fluoro-1-methoxy-[1,2,4]triazolo[4,3-a]quinoxaline, 420 mg of 4-methoxybenzylamine, and 1.02 g of triethylamine in DMF (10 mL) was stirred at room temperature for 72 hrs. The reaction mixture was diluted with methylene chloride, and washed with water. The organic emulsions were collected and concentrated, and the residue was separated by silica gel chromatography to provide a white solid.

Step B

The product of Step A was suspended in a 1:1 mixture of MeOH/chloroform (10 mL), and 33 equiv. of trifluoroacetic acid was added. The yellow solution was heated to reflux for 18 hrs., and then concentrated to a yellow solid. The residue was dissolved in AcOH (6.5 equiv.), and 30 equiv. of 48% aqueous HBr was added, followed by heating to reflux for four hrs. The reaction was cooled to room temperature, and a brown solid was collected by filtration. This was dissolved in 10% MeOH/EtOAc, and washed with water, dried over sodium sulfate, filtered, and concentrated to leave a white solid.

Step C

A slurry of 17 mg of the product of Step B in chloroform (0.5 mL) was stirred as 73 mg of triethylamine and 55 mg of acetyl chloride were added. After stirring for 24 hrs., the reaction was concentrated, the residue suspended in 10% IPA/EtOAc, and washed with water. The organic emulsion was concentrated to a yellow solid that was triturated to afford the bis-acetylated product as an off-white solid.

Step D

A solution of 9 mg of the product of Step C in a 1:5 chloroform/MeOH mixture was stirred at room temperature for 24 hrs. The reaction mixture was concentrated to provide the title compound as an off-white solid. MS $(M+H)^+=262.0$.

EXAMPLE 82

4-(Isopronylamino)-1-oxo-1,2-dihydro-[1,2,4]triazolo[4,3-a]quinoxalin-7-carboxylic acid Step A A mixture of methyl-3,4-diaminobenzoate (4.5 g) in diethyloxalate (50 mL) was heated at reflux for three hrs. After cooling to 23° C., the solid was isolated by filtration, affording 2,3-dioxo-1,2,3,4-tetrahydro-quinoxaline-6-carboxylic acid methyl ester as a light yellow solid. MS $(M-H)^-=219.1$.

Step B

DMF (5 drops) was added to a suspension of 2,3-dioxo-1,2,3,4-tetrahydro-quinoxaline-6-carboxylic acid methyl ester (650 mg) in thionyl chloride (6.7 mL) at 23° C. The reaction mixture was then heated to reflux for 18 hrs. After cooling to 23° C. and concentration, the residue was dissolved in chloroform and washed sequentially with portions of saturated aqueous sodium bicarbonate and brine. Drying over sodium sulfate and concentration afforded 2,3-dichloro-quinoxaline-6-carboxylic acid methyl ester as a white solid. MS $(M+H)^+=257.1$.

Step C

Hydrazine monohydrate (0.26 mL) was added dropwise to a suspension of 2,3-dichloro-quinoxaline-6-carboxylic acid methyl ester (1.2 g) in methanol (10 mL) at −10° C. After three hrs. at this temperature, an additional portion of hydrazine monohydrate (0.26 mL) was added, and the resulting mixture was stirred at 0° C. for three hrs., and then for one hr. at 23° C. The suspension was filtered, and the solids were washed with MeOH. Flash column chromatography provided a residue that was recrystallized from MeOH to provide 3-chloro-2-hydrazino-quinoxaline-6-carboxylic acid methyl ester as a yellow solid. MS $(M+H)^+=253.2$.

Step D

A solution of 3-chloro-2-hydrazino-quinoxaline-6-carboxylic acid methyl ester (890 mg) in tetramethylorthocarbonate (10 mL) was heated at 100° C. for three hrs. After cooling to 23° C., the precipitated solid was isolated by filtration and rinsed with EtOAc, providing 4-chloro-1-methoxy-[1,2,4]triazolo[4,3-a]quinoxaline-7-carboxylic acid methyl ester as an orange solid. MS $(M+H)^+=293.2$.

Step E

A mixture of 4-chloro-1-methoxy-[1,2,4]triazolo[4,3-a]quinoxaline-7-carboxylic acid methyl ester (80 mg), isopropylamine (24 mg) and sodium bicarbonate (45 mg) in DMF (2 mL) was stirred at 23° C. for 17 hrs. The mixture was then partitioned between water and EtOAc. The organic layer was washed with brine, dried over sodium sulfate, and concentrated. Trituration with EtOAc/hexanes afforded 4-isopropylamino-1-methoxy-[1,2,4]triazolo[4,3-a]quinoxaline-7-carboxylic acid methyl ester as a light yellow solid. MS (M+H)$^+$=316.3.

Step F

A solution of 4-isopropylamino-1-methoxy-[1,2,4]triazolo[4,3-a]quinoxaline-7-carboxylic acid methyl ester (25 mg) in AcOH (1.0 mL) and hydrobromic acid (0.5 mL) was heated to 100° C. for 90 min. The solution was cooled to 23° C. and concentrated. The resulting residue was purified by trituration to afford the title compound as a light yellow solid. MS (M+H)$^+$=288.3.

EXAMPLE 83

4-Isopropylamino-1-oxo-1,2-dihydro-[1,2,4]triazolo[4,3-a]quinoxaline-8-carboxylic acid methyl ester Step A To a solution of 8-bromo-4-chloro-1-methoxy-[1,2,4]triazolo[4,3-a]quinoxaline (2.0 g) in DMF (50 mL) was added solid sodium bicarbonate (1.1 g) and isopropylamine (0.82 mL). The resulting mixture was stirred at 23° C. for 18 hrs. and then diluted with EtOAc. The mixture was washed sequentially with water and brine, and then dried over sodium sulfate. Concentration afforded (8-bromo-1-methoxy-[1,2,4]triazolo[4,3-a]quinoxalin-4-yl)-isopropyl-amine as a light yellow solid. MS (M+H)$^+$=337.3.

Step B

A solution of 2.0 g of (8-bromo-1-methoxy-[1,2,4]triazolo[4,3-a]quinoxalin-4-yl)-isopropyl-amine, 0.54 g of Pd(II) acetate, 0.66 g of 1,3-bis-(diphenylphosphino)propane, and triethylamine (21 mL) in a 1.1/1.0 mixture of MeOH/DMSO was agitated under an atmosphere of CO (45 psi) at 75° C. for 96 hrs. After cooling to 23° C., the solution was diluted with water and methylene chloride and the resulting mixture filtered through diatomaceous earth. The filtrate was concentrated and the residue was dissolved in methylene chloride and washed with brine (2×). The title compound precipitated from the organic layer upon standing and was isolated by filtration. MS (M+H)$^+$=302.3.

EXAMPLE 84

4-Isopropylamino-1-oxo-1,2-dihydro-[1,2,4]triazolo[4,3-a]quinoxaline-8-carboxylic acid, sodium salt To a suspension of 4-isopropylamino-1-oxo-1,2-dihydro-[1,2,4]triazolo[4,3-a]quinoxaline-8-carboxylic acid methyl ester (1.35 g) in a 2:1 mixture of THF/MeOH (150 mL) was added aqueous sodium hydroxide solution (1 N, 8.96 mL). The resulting solution was heated in an oil bath at 85° C. for 36 hrs., and then cooled and concentrated. The residue was triturated with EtOAc and the title compound was isolated as an off-white solid by filtration and drying. MS (M–H)$^-$=286.3.

EXAMPLE 85

4Isopropylamino-1-oxo-1,2-dihydro-[1,2,4]triazolo[]quinoxaline-8-carboxylic acid-(2-methoxy-ethyl)-methyl-amide To a solution of 4-isopropylamino-1-oxo-1,2-dihydro-[1,2,4]triazolo[4,3-a]quinoxaline-8-carboxylic acid, sodium salt (130 mg), N-(2-methoxyethyl)methylamine (104 mg), and triethylamine (0.12 mL) in EtOAc (5 mL) at 23° C. was added a solution of 1-propanephosphonic acid cyclic anhydride (50 wt. % in ethyl acetate, 0.18 mL). After 24 hrs., the solution was diluted with EtOAc, and washed sequentially with portions of saturated aqueous sodium bicarbonate (2×), and saturated aqueous sodium chloride (2×). The organic layer was dried over sodium sulfate and concentrated. Trituration of the residue afforded a light yellow solid. MS (M+H)$^+$=359.4.

The following compounds of formula (I) were prepared in a manner analogous to that described in Example 85 using appropriate starting materials.

| Example | Name | MS (M + H)$^+$ |
|---|---|---|
| 86 | 4-Isopropylamino-1-oxo-1,2-dihydro-[1,2,4]triazolo[4,3-a]quinoxaline-8-carboxylic acid-(2-methoxy-ethyl)-amide | 345.4 |
| 87 | 4-Isopropylamino-8-(pyrrolidine-1-carbonyl)-2H-[1,2,4]triazolo[4,3-a]quinoxaline-1-one | 341.4 |
| 88 | 4-Isopropylamino-1-oxo-1,2-dihydro-[1,2,4]triazolo[4,3-a]quinoxaline-8-carboxylic acid-benzylamide | 377.4 |
| 89 | 4-Isopropylamino-1-oxo-1,2-dihydro-[1,2,4]triazolo[4,3-a]quinoxaline-8-carboxylic acid-benzyl-methyl-amide | 391.4 |
| 90 | 4-Isopropylamino-1-oxo-1,2-dihydro-[1,2,4]triazolo[4,3-a]quinoxaline-8-carboxylic acid-methyl-pyridin-4-ylmethyl-amide | 392.4 |
| 91 | 4-Isopropylamino-1-oxo-1,2-dihydro-[1,2,4]triazolo[4,3-a]quinoxaline-8-carboxylic acid-diethylamide | 343.4 |
| 92 | 4-Isopropylamino-8-(morpholine-1-carbonyl)-2H-[1,2,4]triazolo[4,3-a]quinoxaline-1-one | 357.4 |
| 93 | 4-Isopropylamino-1-oxo-1,2-dihydro-[1,2,4]triazolo[4,3-a]quinoxaline-8-carboxylic acid-dimethylamide | 315.0 |
| 94 | 4-Isopropylamino-1-oxo-1,2-dihydro-[1,2,4]triazolo[4,3-a]quinoxaline-8-carboxylic acid-methylamide | 301.0 |
| 95 | 8-(Azetidine-1-carbonyl)-4-isopropylamino-2H-[1,2,4]triazolo[4,3-a]quinoxaline-1-one | 327.0 |
| 96 | 4-Isopropylamino-1-oxo-1,2-dihydro-[1,2,4]triazolo[4,3-a]quinoxaline-8-carboxylic acid-isobutylamide | 343.0 |
| 97 | 4-Isopropylamino-1-oxo-1,2-dihydro-[1,2,4]triazolo[4,3-a]quinoxaline-8-carboxylic acid-propylamide | 329.0 |
| 98 | 4-Isopropylamino-1-oxo-1,2-dihydro-[1,2,4]triazolo[4,3-a]quinoxaline-8-carboxylic acid-cyclopropylmethylmethylamide | 341.0 |
| 99 | 4-Isopropylamino-1-oxo-1,2-dihydro-[1,2,4]triazolo[4,3-a]quinoxaline-8-carboxylic acid-(2-isopropoxy-ethyl)-amide | 373.0 |
| 100 | 4-Isopropylamino-1-oxo-1,2-dihydro-[1,2,4]triazolo[4,3-a]quinoxaline-8-carboxylic acid-(2-phenyl-ethyl)-amide | 391.0 |
| 101 | 4-Isopropylamino-1-oxo-1,2-dihydro-[1,2,4]triazolo[4,3-a]quinoxaline-8-carboxylic acid-cyclohexylmethyl-amide | 383.0 |
| 102 | 4-Isopropylamino-1-oxo-1,2-dihydro-[1,2,4]triazolo[4,3-a]quinoxaline-8-carboxylic acid-(2-morpholin-4-yl-ethyl)-amide | 400.0 |
| 103 | 4-Isopropylamino-1-oxo-1,2-dihydro-[1,2,4]triazolo[4,3-a]quinoxaline-8-carboxylic acid-(1,1-dimethyl-propyl)-amide | 357.0 |

-continued

| Example | Name | MS (M + H)+ |
|---|---|---|
| 104 | 4-Isopropylamino-1-oxo-1,2-dihydro-[1,2,4]triazolo[4,3-a]quinoxaline-8-carboxylic acid-(tetrahydro-furan-2-ylmethyl)-amide | 371.0 |
| 105 | 4-Isopropylamino-1-oxo-1,2-dihydro-[1,2,4]triazolo[4,3-a]quinoxaline-8-carboxylic acid-(thiophen-2-ylmethyl)-amide | 383.0 |

The following compounds of formula (I) were prepared in a manner analogous to that described in Example 85, using 4-isopropylamino-1-methoxy-[1,2,4]triazolo[4,3-a]quinoxaline-7-carboxylic acid.

| Example | Name | MS (M + H)+ or (M − H)− |
|---|---|---|
| 106 | 4-Isopropylamino-7-(4-methylpiperazine-1-carbonyl)-2H-[1,2,4]triazolo[4,3-a]quinoxaline-1-one | 368.4 (−) |
| 107 | 4-Isopropylamino-1-oxo-1,2-dihydro-[1,2,4]triazolo[4,3-a]quinoxaline-7-carboxylic acid-(2-dimethylamino-ethyl)-methyl-amide | 370.4 (−) |
| 108 | 4-Isopropylamino-1-oxo-1,2-dihydro-[1,2,4]triazolo[4,3-a]quinoxaline-7-carboxylic acid-(2-methoxy-ethyl)-methyl-amide | 359.4 (+) |
| 109 | 4-Isopropylamino-1-oxo-1,2-dihydro-[1,2,4]triazolo[4,3-a]quinoxaline-7-carboxylic acid-(2-methoxy-ethyl)-amide | 345.0 (+) |
| 110 | 4-Isopropylamino-1-oxo-1,2-dihydro-[1,2,4]triazolo[4,3-a]quinoxaline-7-carboxylic acid-benzyl-methyl-amide | 391.0 (+) |

EXAMPLE 111

4-Isopropylamino-8-morpholin-4-ylmethyl-2H-[1,2,4]triazolo[4,3-a]quinoxalin-1-one Solid LAH (21 mg) was added to a solution of 4-isopropylamino-8-(morpholine-1-carbonyl)-2H-[1,2,4]triazolo[4,3-a]quinoxaline-1-one (98 mg) in THF (3.0 mL) at 23° C. After stirring for 45 min., the mixture was heated to 50° C. for 60 min. After cooling to 23° C., portions of water (100 μL), 15% aqueous sodium e solution (100 μL), and water (300 μL) were added sequentially. The resulting suspension was filtered through a pad of diatomaceous earth, rinsing with EtOAc. The filtrate was dried over sodium sulfate and concentrated. The resulting residue was triturated with EtOAc/hexanes to afford a solid. The title compound was converted to its hydrochloride salt by dissolution in MeOH, followed by treatment with an excess of an ethereal solution of HCl. Filtration afforded a yellow solid. MS (M+H)+ =343.4.

The following compounds of formula (I) were prepared in a manner analogous to that described in Example 111 using appropriate starting materials.

| Example | Name | MS (M + H)+ |
|---|---|---|
| 112 | 8-[(Benzyl-methyl-amino)-methyl]-4-isopropylamino-2H-[1,2,4]triazolo[4,3-a]quinoxaline-1-one | 377.4 |
| 113 | 8-Dimethylaminomethyl-4-isopropylamino-2H-[1,2,4]triazolo[4,3-a]quinoxalin-1-one | 301.0 |

EXAMPLE 114

1-Oxo-4-(2-pyridin-4-yl-ethylamino)-1,2-dihydro-[1,2,4]triazolo[4,3-a]quinoxaline-7-carboxylic acid Step A A mixture of 4-chloro-1-methoxy-[1,2,4]triazolo[4,3-a]quinoxaline-7-carboxylic acid methyl ester (80 mg), 2-(4-pyridyl)ethylamine (50 mg), and sodium bicarbonate (45 mg) in DMF (2 mL) was stirred at 50° C. for 15 hrs. The mixture was cooled to 23° C., and then diluted with water and EtOAc. A precipitate formed which was isolated by filtration to afford 1-methoxy-4-(2-pyridin-4-ylethylamino)-[1,2,4]triazolo[4,3-a]quinoxaline-7-carboxylic acid methyl ester. MS (M+H)+=379.3.

Step B

A suspension of 1-methoxy-4-(2-pyridin-4-ylethylamino)-[1,2,4]triazolo[4,3-a]quinoxaline-7-carboxylic acid methyl ester (47 mg) in acetic acid (3 mL) and hydrobromic acid (1 mL) was stirred at 23° C. for 60 min., and was then heated to 100° C. for 90 min. After cooling to 23° C., the solution was concentrated and the resulting residue was triturated with MeOH/methylene chloride. Filtration afforded the title compound as a white solid. MS (M+H)+ =351.3.

EXAMPLE 115

1-Oxo-4-(2-pyridin-4-yl-ethylamino)-1,2-dihydro-[1,2,4]triazolo[4,3-a]quinoxaline-7-carboxylic acid methyl ester A solution of 1-methoxy-4-(2-pyridin-4-ylethylamino)-[1,2,4]triazolo[4,3-a]quinoxaline-7-carboxylic acid methyl ester (32 mg) was treated with 48% HBr (4 mL) in AcOH (6 mL) at 23° C. After 2 hrs., the solution was concentrated. Trituration of the residue with MeOH/methylene chloride, followed by filtration, afforded a light yellow solid. MS (M+H)+=365.3.

The following compounds of formula (I) were prepared in a manner analogous to that described in Example 115 using appropriate starting materials.

| Example | Name | MS (M + H)+ |
|---|---|---|
| 116 | 1-Oxo-4-[2-(4-trifluoromethyl-pyridin-2-ylamino)-ethylamino]-1,2-dihydro-[1,2,4]triazolo[4,3-a]quinoxaline-7-carboxylic acid methyl ester | 448.4 |
| 117 | 4-[2-(Benzothiazol-2-ylamino)-ethylamino]-1-oxo-1,2-dihydro-[1,2,4]triazolo[4,3-a]quinoxaline-7-carboxylic acid methyl ester | 436.3 |

-continued

| Example | Name | MS (M + H)+ |
|---|---|---|
| 118 | 4-Isopropylamino-1-oxo-1,2-dihydro-[1,2,4]triazolo[4,3-a]quinoxaoline-7-carboxylic acid methyl ester | 302.2 |
| 119 | 4-[2-(Benzooxazol-2-ylamino)-ethylamino]-1-oxo-1,2-dihydro-[1,2,4]triazolo[4,3-a]quinoxaline-7-carboxylic acid methyl ester | 420.4 |

EXAMPLE 120

8-Hydroxymethyl-4-isopropylamino-2H-[1,2,4]triazolo[4,3-a]quinoxalin-1-one

A solution of 4-isopropylamino-1-oxo-1,2-dihydro-[1,2,4]triazolo[4,3-a]quinoxaline-8-carboxylic acid methyl ester (200 mg) in THF (5.0 mL) was stirred as LAH (76 mg) was added. The mixture was heated to 65° C. for two hr. and cooled to 23° C. prior to quenching with water (100 µL), 15% sodium hydroxide (100 µL); and water (300 µL). The solids were removed by filtration through diatomaceous earth, and the filtrate was concentrated. The residue was purified by silica gel chromatography to provide the title compound as a white solid. MS (M+H)+=329.0.

EXAMPLE 121

4-Isopropylamino-8-methyl-2H-[1,2,4]triazolo[4,3-a]quinoxalin-1-one

A solution of 8-hydroxymethyl-4-isopropylamino-2H-[1,2,4]triazolo[4,3-a]quinoxalin-1-one (20 mg) in EtOH (15 mL) was treated 10% Pd/C (10 mg), and the mixture was agitated under 45 psi hydrogen atmosphere for 68 hrs. The reaction mixture was filtered through diatomaceous earth, the filtrate concentrated, and the residue purified by silica gel chromatography to provide the title compound as a solid. MS (M+H)+=258.0.

EXAMPLE 122

4-Isopropylamino-1-oxo-1,2-dihydro-[1,2,4]triazolo[4,3-a]quinoxaline-7-carboxylic acid-methoxy-methyl-amide A mixture of 4-isopropylamino-1-oxo-1,2-dihydro-[1,2,4]triazolo[4,3-a]quinoxaline-7-carboxylic acid (130 mg), N,O-dimethylhydroxylamine hydrochloride (39 mg), HOBT (54 mg), and EDC (77 mg) in DMF (4.0 mL) was stirred at 23° C. for 20 hrs. The solution was then diluted with EtOAc and washed sequentially with saturated aqueous sodium bicarbonate and saturated aqueous sodium chloride solutions. The organic layer was dried over sodium sulfate, filtered, and the filtrate concentrated to afford the title compound as a light yellow solid. MS (M+H)+=331.6.

EXAMPLE 123

4-Isopropylamino-7-(4-methyl-piperazin-1-ylmethyl)-2H-[1,2,4]triazolo[4,3-a]quinoxalin-1-one Step A
Solid LAH (7 mg) was added to a solution of (4-isopropylamino-1-methoxy-[1,2,4]triazolo[4,3-a]quinoxalin-7-yl)-(4-methyl-piperazin-1-yl)-methanone (45 mg) in THF (2.0 mL) at 23° C. After 60 min., water (40 µL), 15% aqueous sodium hydroxide solution (40 µL), and water (120 µL) were added sequentially, and the mixture was dried over sodium sulfate and concentrated. The residue was purified by silica gel chromatography to afford the amine product as a yellow residue. MS (M+H)+=370.4.

Step B
A solution of isopropyl-[1-methoxy-7-(4-methyl-piperazin-1-ylmethyl)-[1,2,4]triazolo[4,3-a]quinoxalin-4-yl] amine (12 mg) in AcOH (1 mL) and 48% HBr (0.5 mL) was stirred at 23° C. for 90 min., then was heated to 90° C. for 100 min. After cooling to 23° C., the solution was concentrated. The resulting residue was concentrated from toluene. Trituration of the residue with MeOH/EtOAc afforded the title compound as a light yellow solid. MS (M+H)+=356.4.

EXAMPLE 124

4-Isopropylamino-7-{[(2-methoxy-ethyl)-methylamino]-methyl}-2H-[1,2,4]triazolo[4,3-a]quinoxalin-1-one Solid LAH (9 mg) was added to a solution of 4-isopropylamino-1-oxo-1,2-dihydro-[1,2,4]triazolo[4,3-a]quinoxaline-7-carboxylic acid-(2-methoxy-ethyl)-methyl-amide (65 mg) in THF (10 mL) at 23° C. The resulting solution was stirred for 75 min. at 23° C., and then for 60 min. at 65° C. An additional portion of LAH (6 mg) was added, and the reaction was heated at 65° C. for an additional 120 min. After cooling to 23° C., portions of water (60 µL), 15% aqueous sodium hydroxide solution (60 µL), and water (120 µL) were added sequentially. The mixture was filtered through a pad of diatomaceous earth, and the filtrate was dried over sodium sulfate and concentrated. The residue was dissolved in MeOH and treated with an excess of HCl (1N in ether) to effect cleavage of the methyl ether. The hydrochloride salt was isolated as a yellow solid after concentration. MS (M−H)−=343.3.

EXAMPLE 125

4-Isopropylamino-7-morpholin-4-ylmethyl-2H-[1,2,4]triazolo[4,3-a]quinoxalin-1-one Step A
Aqueous sodium hydroxide solution (1N, 0.40 mL) was added to a solution of 4-isopropylamino-1-methoxy[1,2,4]triazolo[4,3-a]quinoxaline-7-carboxylic acid methyl ester (126 mg) in THF (3 mL) and MeOH (1.5 mL). The reaction solution was stirred at 23° C. for two hrs., and then at 50° C. for three hrs. The solution was cooled to 23° C. and was held at that temperature for an additional 16 hrs. Concentration afforded a residue that was triturated with EtOAc/hexanes to afford 4-isopropylamino-1-methoxy-[1,2,4]triazolo[4,3-a]quinoxaline-7-carboxylic acid, sodium salt as a light yellow solid. MS (M+H)+=302.4.

Step B
A mixture of 4-isopropylamino-1-methoxy-[1,2,4]triazolo[4,3-a]quinoxaline-7-carboxylic acid (127 mg), N,O-dimethylhydroxylamine hydrochloride (41 mg), 1-hydroxy-7-azabenzotriazole (57 mg), and EDC (81 mg) in DMF (2.0 mL) was stirred at 23° C. for 12 hrs. The solution was then diluted with EtOAc and washed sequentially with saturated aqueous sodium bicarbonate and saturated aqueous sodium chloride (2×) solutions. The organic layer was dried over sodium sulfate. The residue was purified by flash chromatography to afford 4-isopropylamino-1-methoxy-[1,2,4]triazolo[4,3-a]quinoxaline-7-carboxylic acid-methoxy-methyl-amide. MS (M+H)$^+$=345.7.

Step C

Solid LAH (8 mg) was added to a solution of 4-isopropylamino-1-methoxy-[1,2,4]triazolo[4,3-a]quinoxaline-7-carboxylic acid-methoxy-methyl-amide (50 mg) in THF at −78° C. After 80 min., the solution was warmed to 23° C. Portions of water (40 μL), 15% aqueous sodium hydroxide solution (40 μL), and water (180 μL) were added sequentially. The resulting mixture was diluted with EtOAc, and was then dried over sodium sulfate and filtered. Concentration afforded 4-isopropylamino-1-methoxy-[1,2,4]triazolo[4,3-a]quinoxaline-7-carbaldehyde as a white solid. MS (M+H)$^+$=286.4.

Step D

Solid sodium triacetoxyborohydride (59 mg) and morpholine (15 μL) were added to a solution of 4-isopropylamino-1-methoxy-[1,2,4]triazolo[4,3-a]quinoxaline-7-carbaldehyde (50 mg) in 1,2-dichloroethane (1.0 mL). The resulting suspension was stirred at 23° C. for 2.5 hrs., and then a portion of AcOH (10 μL) was added. After an additional 2.5 hrs., the reaction mixture was concentrated. The residue was partitioned between methylene chloride and a saturated aqueous solution of sodium bicarbonate. The organic layer was washed with brine, dried over sodium sulfate and concentrated. Silica gel chromatography afforded isopropyl-(1-methoxy-7-morpholin-4-ylmethyl-[1,2,4]triazolo[4,3-a]quinoxalin-4-yl)-amine as a white solid. MS (M+H)$^+$=357.5.

Step E

A solution of isopropyl-(1-methoxy-7-morpholin-4-ylmethyl-[1,2,4]triazolo[4,3-a]quinoxalin-4-yl)-amine (32 mg) in AcOH (0.5 mL) and 48% HBr (0.5 mL) was heated at 50° C. for 2.5 hrs. After cooling to 23° C., the solution was concentrated. The resulting residue was concentrated from toluene, and then triturated with MeOH/EtOAc. The resulting solid was isolated by filtration, and then concentrated from MeOH to afford a light yellow solid. MS (M+H)$^+$=341.3.

The following compound of formula (I) was prepared in a manner analogous to that described in Example 125 using appropriate starting materials.

| Example | Name | MS (M + H)$^+$ |
|---|---|---|
| 126 | 7-Dimethylaminomethyl-4-isopropylamino-2H-[1,2,4]triazolo[4,3-a]quinoxalin-1-one | 299.4 |

EXAMPLE 127

8-[(2-Isopropoxy-ethylamino)-methyl]-4-isopropylamino-2H-[1,2,4]triazolo[4,3-a]quinoxalin-1-one A suspension of 30 mg of 4-isopropylamino-1-oxo-1,2-dihydro-[1,2,4]triazolo[4,3-a]quinoxaline-8-carboxylic acid-(2-isopropoxy-ethyl)-amide in THF (5.0 mL) was stirred as sodium borohydride (30 mg) was added. This mixture was heated to reflux and then boron trifluoride etherate (0.15 mL) was added dropwise. The mixture was refluxed for two hr. and then cooled to 23° C. and acidified to pH 3.0 with 3N HCl. After stirring for 30 min., the reaction was diluted with methylene chloride and basified to pH 14 with 6N sodium hydroxide. The layers were separated and the aqueous was extracted with methylene chloride and the combined organic layers were dried over sodium sulfate, filtered, and concentrated. Purification of the residue by silica gel chromatography provided the product as a white solid. MS (M+H)$^+$=359.0.

The following compound of formula (I) was prepared in a manner analogous to that described in Example 127 using appropriate starting materials.

| Example | Name | MS (M + H)$^+$ |
|---|---|---|
| 128 | 8-(Isobutylamino-methyl)-4-isopropylamino-2H-[1,2,4]triazolo[4,3-a]quinoxalin-1-one | 329.0 |

Biological Methodologies

GSK-3 Inhibition

The specific activities of the compounds of formula (I) in inhibiting GSK-3 can be determined in both cell-free and cell-based assays, both of which have been previously described in the relevant art. See, for example, U.S. Pat. Nos. 6,417,185 and 6,489,344, the disclosures of which are incorporated herein by reference in their entirety.

A cell-free testing assay can be generally carried out by incubating GSK-3 with a peptide substrate, radiolabeled ATP (e.g., for example, $\gamma^{33}$P-c$\gamma^{32}$P-ATP, both of which are available from Amersham; Arlington Heights, Ill.), magnesium ions, and the compound to be assayed. The mixture is incubated for a period of time to allow incorporation of radiolabeled phosphate into the peptide substrate by GSK-3 activity. The reaction mixture is then washed to remove unreacted radiolabeled ATP, typically after first transferring all or a portion of the enzyme reaction mixture to a well that contains a uniform amount of a ligand capable of binding to the peptide substrate. The amount of $\gamma^{33}$P or $\gamma^{32}$P remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, described in Wang, et al., Anal. Biochem., 220, 397402 (1994). Purified GSK-3 for a testing assay may, for example, be obtained from cells transfected with a human GSK-3β expression plasmid as described in, for example, Stambolic, et al., Current Biology, 6, 1664–1668 (1996).

Another example of a GSK-3 testing assay, similar to the one described hereinabove, is as follows: enzyme activities are assayed as the incorporation of $^{33}$P from the gamma phosphate of $^{33}$P-ATP (Amersham; Arlington Heights, Ill.; catalog #AH-9968) into biotinylated peptide substrate PKTP-KKAKKL. The reactions are carried out in a buffer containing 50 mM tris-HCl, pH 8.0; 10 mM MgCl$_2$, 0.1 mM Na$_3$VO$_4$, and 1 mM DTT. The final concentration of ATP is 0.5 μM (final specific radioactivity of 4 μCi/nmol), and the final concentration of substrate is 0.75 μM. The reactions, initiated by the addition of enzyme, are carried out at room temperature for about 60 minutes. The reactions are stopped by addition of 0.6 volume of buffer containing (final concentrations): 2.5 mM EDTA, 0.05% Triton-X 100, 100 μM ATP, and 1.25 mg/ml streptavidin-coated SPA beads (Amersham; Arlington Heights, Ill.; catalog #RPNQ0007). Radioactivity associated with the beads is then quantified by standard scintillation counting.

A generally preferred GSK-3 testing assay, similar to the one described hereinabove, is as follows: enzyme activities are assayed as the incorporation of $^{33}P$ from the gamma phosphate of $^{33}P$-ATP (Amersham; Arlington Heights, Ill.; catalog #AH-9968) into biotinylated peptide substrate Biotin-SRHSSPHQpSEDEEE-OH (AnaSpec Inc., San Jose, Calif.). The reactions are carried out in a buffer containing 8 mM MOPS; 10 mM Mg(OAc)$_2$, 0.2 mM EDTA (pH 7.0), and 1 mM DTT. The final concentration of ATP is 2.0 μM (final specific radioactivity of 4 μCi/nmol), and the final concentration of substrate is 1.0 μM. The reactions, initiated by the addition of enzyme, are carried out at room temperature for about 75 minutes. The reactions are stopped by addition of 0.6 volume of buffer containing (final concentrations): 0.05 mM EDTA, 0.1% Triton-X 100, 100 μM ATP, and 2.5 mg/ml streptavidin-coated SPA beads. Radioactivity associated with the beads is then quantified by standard scintillation counting.

The compounds of formula (I) generally exhibit inhibitory activity, expressed as $IC_{50}$'s, against GSK-3 that are <10,000 nM. Generally preferred compounds have $IC_{50}$'s<200 nM. For example, the compound 8-fluoro-4-[2-(5-trifluoromethyl-pyridin-2-ylamino)-ethylamino]-2H-[1,2,4]triazolo[4,3-a]quinoxaline-1-one has an $IC_{50}$ of 6 nM.

The invention claimed is:

1. A compound of formula (I)

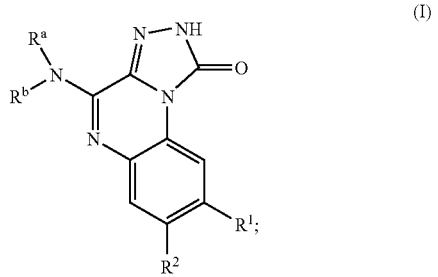

or a pharmaceutically acceptable salt thereof wherein:
  $R^a$ and $R^b$ are, independently:
  (i) hydrogen;
  (ii) acetyl;
  (iii) —(C$_1$–C$_6$)alkyl, optionally, and independently, substituted with from 1–3 of:
    (a) halogen; (b) —NR$^3$R$^4$; (c) —COR$^5$; (d) —OR$^6$; (e) aryl, optionally, and independently, substituted with from 1–3 of halogen; —(C$_1$–C$_6$)alkyl; or —(C$_1$–C$_6$)alkoxy; (f) heteroaryl, optionally, and independently, substituted with from 1–3 of trifluoromethyl or —(C$_1$–C$_6$)alkyl; (g) —(C$_3$–C$_{11}$)cycloalkyl; or (h) —(C$_3$–C$_{11}$)heterocycloalkyl, optionally, and independently, substituted with from 1–3 of —(C$_1$–C$_6$)alkyl or —(C$_1$–C$_6$)alkoxy; wherein:
    $R^3$ and $R^4$ are independently:
    (j) hydrogen; (k) amidino; (l) aryl, optionally, and independently, substituted with from 1–3 of halogen; cyano; nitro; —(C$_1$–C$_6$)alkyl, —(C$_1$–C$_6$)alkoxy, or —COR$^5$; (m) —(C$_1$–C$_6$)alkyl, optionally, and independently, substituted with from 1–3 of —(C$_3$–C$_{11}$)heterocycloalkyl; —(C$_3$–C$_{11}$)cycloalkyl; —(C$_1$–C$_6$)alkoxy; aryl; or heteroaryl; (n) heteroaryl, optionally, and independently, substituted with from 1–3 of halogen; trifluoromethyl; cyano; nitro; —COR$^5$; —(C$_1$–C$_6$)alkyl, optionally substituted with —(C3–C$_{11}$)heterocycloalkyl; or —(C$_1$–C$_6$)alkoxy; (o) —(C$_3$–C$_{11}$)heterocycloalkyl, optionally substituted with from 1–3 of —(C$_1$–C$_6$)alkyl; or (p) —COR$^5$;

$R^5$ is (q) hydroxy; (r) —(C$_1$–C$_6$)alkyl, optionally, and independently, substituted with from 1–3 of —(C$_1$–C$_6$) alkoxy or aryl; (s) —(C$_1$–C$_6$)alkoxy; (t) heteroaryl; or (u) —(C$_3$–C$_{11}$)heterocycloalkyl, optionally substituted with from 1–3 of —(C$_1$–C$_6$)alkyl; and $R^6$ is (v) —(C$_1$–C$_6$)alkyl, optionally, and independently, substituted with from 1–3 of —(C$_1$–C$_6$)alkoxy or aryl; (w) heteroaryl; or (x) —(C$_3$–C$_{11}$)heterocycloalkyl, optionally substituted with from 1–3 of —(C$_1$–C$_6$) alkyl;
  (iv) —(C$_3$–C$_{11}$)cycloalkyl; or
  (v) —(C$_3$–C$_{11}$)heterocycloalkyl, optionally, and independently, substituted with from 1–3 of halogen; —COR$^5$; —(C$_1$–C$_6$)alkyl; and —(C$_1$–C$_6$)alkoxy; or $R^a$ and $R^b$, taken together with the nitrogen atom to which they are attached, form a 5- or 6-membered heterocycloalkyl ring, optionally having from 1–3 additional heteroatoms independently selected from the group consisting of nitrogen, oxygen, and sulfur, wherein said 5- or 6-membered heterocycloalkyl ring is optionally, and independently, substituted with from 1–3 of halogen; —(C$_1$–C$_6$)alkyl; or heteroaryl, optionally, and independently, substituted with from 1–3 of halogen; trifluoromethyl; and cyano; and $R^1$ and $R^2$ are independently selected from the group consisting of amino; halogen; hydrogen; trifluoromethyl; nitro; —COR$^5$; —NR$^3$R$^4$; —CONR$^3$R$^4$; and —(C$_1$–C$_6$)alkyl, optionally, and independently, substituted with from 1–3 of —(C$_3$–C$_{11}$)heterocycloalkyl; —NR$^3$R$^4$; aryl; heteroaryl; or hydroxy;
  provided that when $R^a$ is hydrogen, and $R^b$ is hydrogen or isopropyl, $R^1$ is not halogen.

2. A compound of claim 1, wherein:
  $R^a$ is hydrogen;
  $R^b$ is selected from the group consisting of (iii) —(C$_1$–C$_6$) alkyl, optionally substituted with: (b) —NR$^3$R$^4$, wherein $R^3$ is hydrogen and $R^4$ is heteroaryl, optionally, and independently, substituted with from 1–3 of trifluoromethyl; cyano; —(C$_1$–C$_6$)alkyl, optionally substituted with —(C$_3$–C$_{11}$)heterocycloalkyl; —(C$_1$–C$_6$) alkoxy; or —COR$^5$; (e) aryl, optionally substituted with from 1–3 halogen atoms; (f) heteroaryl; (h) —(C$_3$–C$_{11}$)heterocycloalkyl; (iv) —(C$_3$–C$_{11}$)cycloalkyl; or (v) —(C$_3$–C$_{11}$)heterocycloalkyl;
  $R^1$ is hydrogen; halogen; —COR$^5$; —CONR$^3$R$^4$; or —(C$_1$–C$_6$)alkyl, optionally, and independently, substituted with from 1–3 of —(C$_3$–C$_{11}$)heterocycloalkyl or —NR$^3$R$^4$; and
  $R^2$ is hydrogen; —CONR$^3$R$^4$; or —(C$_1$–C$_6$)alkyl, optionally, and independently, substituted with from 1–3 of —(C$_3$–C$_{11}$)heterocycloalkyl or —NR$^3$R$^4$.

3. A compound of claim 1, wherein:
  $R^a$ is hydrogen;
  $R^b$ is (iii) —(C$_1$–C$_3$)alkyl, optionally substituted with (b) —NR$^3$R$^4$, wherein $R^3$ is hydrogen and $R^4$ is heteroaryl, optionally, and independently, substituted with from 1–3 of trifluoromethyl; cyano; —(C$_1$–C$_6$)alkyl, optionally substituted with —(C$_3$–C$_{11}$)heterocycloalkyl; or —(C$_1$–C$_6$)alkoxy; (e) aryl; (f) heteroaryl; (h) —(C$_3$–C$_6$)heterocycloalkyl; (iv) —(C$_3$–C$_6$)cycloalkyl; or (v) —(C$_3$–C$_{11}$)heterocycloalkyl;

R$^1$ is hydrogen; fluoro; chloro; bromo; —COR$^5$, wherein R$^5$ is hydroxy or —(C$_1$–C$_6$)alkyl; or —CONR$^3$R$^4$, wherein R$^3$ is hydrogen or —(C$_1$–C$_6$)alkyl; and R$^4$ is —(C$_1$–C$_6$)alkyl, optionally substituted with —(C$_1$–C$_6$)alkoxy; and R$^2$ is hydrogen or —CONR$^3$R$^4$, wherein R$^3$ is —(C$_1$–C$_6$)alkyl; and R$^4$ is —(C$_1$–C$_6$)alkyl, optionally substituted with —(C$_1$–C$_6$)alkoxy.

4. A compound of claim 1 selected from the group consisting of:

8-fluoro-4-cyclohexylamino-2H-[1,2,4]triazolo[4,3-a]quinoxaline-1-one;
8-fluoro-4-(piperidin-4-ylamino)-2H-[1,2,4]triazolo[4,3-a]quinoxaline-1-one;
8-fluoro-4-(4-phenyl-propylamino)-2H-[1,2,4]triazolo[4,3-a]quinoxaline-1-one;
4-isopropylamino-1-oxo-1,2-dihydro-[1,2,4]triazolo[4,3-a]quinoxalin-8-carboxylic acid-(2-methoxy-ethyl)-amide;
4-isopropylamino-1-oxo-1,2-dihydro-[1,2,4]triazolo[4,3-a]quinoxalin-8-carboxylic acid-dimethylamide;
4-isopropylamino-1-oxo-1,2-dihydro-[1,2,4]triazolo[4,3-a]quinoxalin-7-carboxylic acid-methylamide;
4-isopropylamino-1-oxo-1,2-dihydro-[1,2,4]triazolo[4,3-a]quinoxalin-8-carboxylic acid-isobutyl amide;
4-isopropylamino-1-oxo-1,2-dihydro-[1,2,4]triazolo[4,3-a]quinoxalin-7-carboxylic acid-(2-methoxy-ethyl)-methyl amide;
4-isopropylamino-1-oxo-1,2-dihydro-[1,2,4]triazolo[4,3-a]quinoxalin-8-carboxylic acid, sodium salt;
4-[2-(1H-benzoimidazol-2-yl)-butylamino]-8-fluoro-2H-[1,2,4]triazolo[4,3-a]quinoxaline-1-one;
4-[2-(1H-benzoimidazol-2-y)-ethylamino]-8-fluoro-2H-[1,2,4]triazolo[4,3-a]quinoxaline-1-one;
4-[2-(1H-benzoimidazol-2-ylamino)-ethylamino]-8-fluoro-2H-[1,2,4]triazolo[4,3-a]quinoxaline-1-one;
4-[2-(benzooxazol-2-ylamino)-ethylamino]-8-chloro-2H-[1,2,4]triazolo[4,3-a]quinoxaline-1-one;
4-[2-(benzothiazol-2-ylamino)-ethylamino]-8-bromo-2H-[1,2,4]triazolo[4,3-a]quinoxaline-1-one;
4-[2-(benzothiazol-2-ylamino)-ethylamino]-8-chloro-2H-[1,2,4]triazolo[4,3-a]quinoxaline-1-one;
4-[2-(1H-benzothiazol-2-ylamino)-ethylamino]-8-fluoro-2H-[1,2,4]triazolo[4,3-a]quinoxaline-1-one;
4-[2-(1H-benzoimidazol-2-y)-propylamino]-8-fluoro-2H-[1,2,4]triazolo[4,3-a]quinoxaline-1-one;
2-[2-(8-fluoro-1-oxo-1,2-dihydro-[1,2,4]triazolo[4,3-a]quinoxalin-4-ylamino)-ethylamino]-isonicotinic acid;
4-[2-(6-methoxy-benzothiazol-2-ylamino)-ethylamino]-2H-[1,2,4]triazolo[4,3-a]quinoxaline-1-one;
8-bromo-4-[2-(1H-indol-3-yl)-ethylamino]-2H-[1,2,4]triazolo[4,3-a]quinoxaline-1-one;
8-fluoro-4-(tetrahydro-pyran-4-ylamino)-2H-[1,2,4]triazolo[4,3-a]quinoxaline-1-one;
8-fluoro-4-[2-(1H-indol-3-yl)-ethylamino]-2H-[1,2,4]triazolo[4,3-a]quinoxaline-1-one;
8-fluoro-4-[2-(pyridin-2-ylamino)-ethylamino]-2H-[1,2,4]triazolo[4,3-a]quinoxaline-1-one;
8-fluoro-4-[2-(pyrimidin-2-ylamino)-ethylamino]-2H-[1,2,4]triazolo[4,3-a]quinoxaline-1-one;
8-fluoro-4-[2-(quinolin-2-ylamino)-ethylamino]-2H-[1,2,4]triazolo[4,3-a]quinoxaline-1-one;
8-fluoro-4-[2-(2-trifluoromethyl-quinolin-4-ylamino)-ethylamino]-2H-[1,2,4]triazolo[4,3-a]quinoxaline-1-one;
8-fluoro-4-[2-(3-trifluoromethyl-pyridin-2-ylamino)-ethylamino]-2H-[1,2,4]triazolo[4,3-a]quinoxaline-1-one;
8-fluoro-4-[2-(4-morpholin-4-ylmethyl-pyridin-2-ylamino)-ethylamino]-2H-(1,2,4]triazolo[4,3-a]quinoxaline-1-one;
8-fluoro-4-[2-(4-trifluoromethyl-pyridin-2-ylamino)-ethylamino]-2H-(1,2,4]triazolo[4,3-a]quinoxaline-1-one;
8-fluoro-4-[2-(4-trifluoromethyl-pyrimidin-2-ylamino)-ethylamino]-2H-[1,2,4]triazolo[4,3-a]quinoxaline-1-one;
8-fluoro-4-[2-(4-trifluoromethyl-pyridin-2-ylamino)-propylamino]-2H-[1,2,4]triazolo[4,3-a]quinoxaline-1-one;
8-fluoro-4-[2-(5-cyano-pyridin-2-ylamino)-ethylamino]-2H-[1,2,4]triazolo[4,3-a]quinoxaline-1-one;
8-fluoro-4-[2-(5-trifluoromethyl-pyridin-2-ylamino)-ethylamino]-2H-[1,2,4]triazolo[4,3-a]quinoxaline-1-one;
8-fluoro-4-[2-(5-trifluoromethyl-pyridin-2-ylamino)-propylamino]-2H-[1,2,4]triazolo[4,3-a]quinoxaline-1-one;
8-fluoro-4-[2-(6-methyl-5,6,7,8-tetrahydro-[1,6]naphthyridin-2-ylamino)-ethylamino]-2H-[1,2,4]triazolo[4,3-a]quinoxaline-1-one;
8-fluoro-4-[2-(6-trifluoromethyl-pyridin-2-ylamino)-ethyl]-amino-2H-[1,2,4]triazolo[4,3-a]quinoxaline-1-one;
8-fluoro-4-[2-(7-trifluoromethyl-quinolin-4-ylamino)-ethylamino]-2H-[1,2,4]triazolo[4,3-a]quinoxaline-1-one;
8-fluoro-4-[2-(8-trifluoromethyl-quinolin-4-ylamino)-ethylamino]-2H-[1,2,4]triazolo[4,3-a]quinoxaline-1-one;
8-fluoro-4-[3-(5-trifluoromethyl-pyridin-2-ylamino)-propylamino]-2H-[1,2,4]triazolo[4,3-a]quinoxaline-1-one; or
1-oxo-4-[2-(4-trifluoromethyl-pyridin-2-ylamino)-ethylamino]-1,2-dihydro-[1,2,4]triazolo[4,3-a]quinoxaline-7-carboxylic acid methyl ester;

or a pharmaceutically acceptable salt thereof.

5. A pharmaceutical composition comprising a compound of claim 1, or a pharmaceutically acceptable salt thereof and a pharmaceutically acceptable carrier, vehicle or diluent.

6. A compound of formula (I)

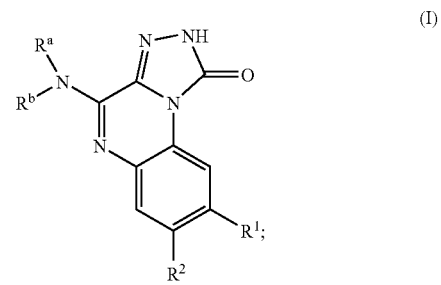

or a pharmaceutically acceptable salt thereof wherein:
R$^a$ is:
(i) hydrogen;
(ii) acetyl;

(iii) —($C_1$–$C_6$)alkyl, optionally, and independently, substituted with from 1–3 of:
(a) halogen; (b) —$NR^3R^4$; (c) —$COR^5$; (d) —$OR^6$; (e) aryl, optionally, and independently, substituted with from 1–3 of halogen; —($C_1$–$C_6$)alkyl; or —($C_1$–$C_6$)alkoxy; (f) heteroaryl, optionally, and independently, substituted with from 1–3 of trifluoromethyl or —($C_1$–$C_6$)alkyl; (g) —($C_3$–$C_{11}$)cycloalkyl; or
(h) —($C_3$–$C_{11}$)heterocycloalkyl, optionally, and independently, substituted with from 1–3 of —($C_1$–$C_6$)alkyl or —($C_1$–$C_6$)alkoxy;

$R^b$ is:
(i) acetyl;
(ii) —($C_1$–$C_6$)alkyl, optionally, and independently, substituted with from 1–3 of:
(a) halogen; (b) —$NR^3R^4$; (c) —$COR^5$; (d) —$OR^6$; (e) aryl, optionally, and independently, substituted with from 1–3 of halogen; —($C_1$–$C_6$)alkyl; or —($C_1$–$C_6$)alkoxy; (f) heteroaryl, optionally, and independently, substituted with from 1–3 of trifluoromethyl or —($C_1$–$C_6$)alkyl; (g) —($C_3$–$C_{11}$)cycloalkyl; or (h) —($C_3$–$C_{11}$)heterocycloalkyl, optionally, and independently, substituted with from 1–3 of —($C_1$–$C_6$)alkyl or —($C_1$–$C_6$)alkoxy;

$R^3$ and $R^4$ independently:
(j) hydrogen; (k) amidino; (l) aryl, optionally, and independently, substituted with from 1–3 of halogen; cyano; nitro; —($C_1$–$C_6$)alkyl, —($C_1$–$C_6$)alkoxy, or —$COR^5$; (m) —($C_1$–$C_6$)alkyl, optionally, and independently, substituted with from 1–3 of —($C_3$–$C_{11}$)heterocycloalkyl; —($C_3$–$C_{11}$)cycloalkyl; —($C_1$–$C_6$)alkoxy; aryl; or heteroaryl; (n) heteroaryl, optionally, and independently, substituted with from 1–3 of halogen; trifluoromethyl; cyano; nitro; —$COR^5$; —($C_1$–$C_6$)alkyl, optionally substituted with —($C_3$–$C_{11}$)heterocycloalkyl; or —($C_1$–$C_6$)alkoxy; (o) —($C_3$–$C_{11}$)heterocycloalkyl, optionally substituted with from 1–3 of —($C_1$–$C_6$)alkyl; or (p) —$COR^5$;

$R^5$ is (q) hydroxy; (r) —($C_1$–$C_6$)alkyl, optionally, and independently, substituted with from 1–3 of —($C_1$–$C_6$)alkoxy or aryl; (s) —($C_1$–$C_6$)alkoxy; (t) heteroaryl; or (u) —($C_3$–$C_{11}$)heterocycloalkyl, optionally substituted with from 1–3 of —($C_1$–$C_6$)alkyl; and $R^6$ is (v) —($C_1$–$C_6$)alkyl, optionally, and independently, substituted with from 1–3 of —($C_1$–$C_6$)alkoxy or aryl; (w) heteroaryl; or (x) —($C_3$–$C_{11}$)heterocycloalkyl, optionally substituted with from 1–3 of —($C_1$–$C_6$)alkyl;
(iv) —($C_3$–$C_{11}$)cycloalkyl; or
(v) —($C_3$–$C_{11}$)heterocycloalkyl, optionally, and independently, substituted with from 1–3 of halogen; —$COR^5$; —($C_1$–$C_6$)alkyl; and —($C_1$–$C_6$)alkoxy; or $R^a$ and $R^b$, taken together with the nitrogen atom to which they are attached, form a 5- or 6-membered heterocycloalkyl ring, optionally having from 1–3 additional heteroatoms independently selected from the group consisting of nitrogen, oxygen, and sulfur, wherein said 5- or 6-membered heterocycloalkyl ring is optionally, and independently, substituted with from 1–3 of halogen; —($C_1$–$C_6$)alkyl; or heteroaryl, optionally, and independently, substituted with from 1–3 of halogen; trifluoromethyl; and cyano; and $R^1$ and $R^2$ are independently selected from the group consisting of amino; halogen; hydrogen; trifluoromethyl; nitro; —$COR^5$; —$NR^3R^4$; —$CONR^3R^4$; and —($C_1$–$C_6$)alkyl, optionally, and independently, substituted with from 1–3 of —($C_3$–$C_{11}$)heterocycloalkyl; —$NR^3R^4$; aryl; heteroaryl; or hydroxy;

provided when $R^a$ is hydrogen, and $R^b$ is isopropyl, $R^1$ is not F, Cl or Br.

7. The compound of claim 6, wherein:
$R^a$ is hydrogen;
$R^b$ is selected from the group consisting of (iii) —($C_1$–$C_6$) alkyl, optionally substituted with: (b) —$NR^3R^4$, wherein $R^3$ is hydrogen and $R^4$ is heteroaryl, optionally, and independently, substituted with from 1–3 of trifluoromethyl; cyano; —($C_1$–$C_6$)alkyl, optionally substituted with —($C_3$–$C_{11}$)heterocycloalkyl; —($C_1$–$C_6$) alkoxy; or —$COR^5$; (e) aryl, optionally substituted with from 1–3 halogen atoms; (f) heteroaryl; (h) —($C_3$–$C_{11}$)heterocycloalkyl; (iv) —($C_3$–$C_{11}$)cycloalkyl; or (v) —($C_3$–$C_{11}$)heterocycloalkyl;
$R^1$ is hydrogen; halogen; —$COR^5$; —$CONR^3R^4$; or —($C_1$–$C_6$)alkyl, optionally, and independently, substituted with from 1–3 of —($C_3$–$C_{11}$)heterocycloalkyl or —$NR^3R^4$; and
$R^2$ is hydrogen; —$CONR^3R^4$; or —($C_1$–$C_6$)alkyl, optionally, and independently, substituted with from 1–3 of —($C_3$–$C_{11}$)heterocycloalkyl or —$NR^3R^4$.

8. The compound of claim 6, wherein:
$R^a$ is hydrogen;
$R^b$ is (iii) —($C_1$–$C_3$)alkyl, optionally substituted with (b) —$NR^3R^4$, wherein $R^3$ is hydrogen and $R^4$ is heteroaryl, optionally, and independently, substituted with from 1–3 of trifluoromethyl; cyano; —($C_1$–$C_6$)alkyl, optionally substituted with —($C_3$–$C_{11}$)heterocycloalkyl; or —($C_1$–$C_6$)alkoxy; (e) aryl; (f) heteroaryl; (h) —($C_3$–$C_6$)heterocycloalkyl; (iv) —($C_3$–$C_6$)cycloalkyl; or (v) —($C_3$–$C_{11}$)heterocycloalkyl;
$R^1$ is hydrogen; fluoro; chloro; bromo; —$COR^5$, wherein $R^5$ is hydroxy or —($C_1$–$C_6$)alkoxy; or —$CONR^3R^4$, wherein $R^3$ is hydrogen or —($C_1$–$C_6$)alkyl; and $R^4$ is —($C_1$–$C_6$)alkyl, optionally substituted with —($C_1$–$C_6$)alkoxy; and
$R^2$ is hydrogen or —$CONR^3R^4$, wherein $R^3$ is —($C_1$–$C_6$)alkyl; and $R^4$ is —($C_1$–$C_6$)alkyl, optionally substituted with —($C_1$–$C_6$)alkoxy.

9. A pharmaceutical composition comprising the compound of claim 6, or a pharmaceutically acceptable slat thereof and a pharmaceutically acceptable carrier, vehicle or diluent.

* * * * *